United States Patent
Shylo et al.

(10) Patent No.: US 9,385,426 B2
(45) Date of Patent: Jul. 5, 2016

(54) METHOD FOR FORMATION OF RADIOMETRIC IMAGES AND AN ANTENNA FOR IMPLEMENTATION OF THE METHOD

(71) Applicant: Radio Physics Solutions, Ltd., Bromesberrow (GB)

(72) Inventors: Sergiy Shylo, Kharkov (UA); Yuriy Sydorenko, Kharkov (UA)

(73) Assignee: Radio Physics Solutions, Ltd., Bromesberro (GB)

( * ) Notice: Subject to any disclaimer, the term of this patent is extended or adjusted under 35 U.S.C. 154(b) by 0 days.

(21) Appl. No.: 14/802,593

(22) Filed: Jul. 17, 2015

(65) Prior Publication Data

US 2015/0320322 A1 Nov. 12, 2015

Related U.S. Application Data

(63) Continuation of application No. 14/457,974, filed on Aug. 12, 2014, now Pat. No. 9,105,960, which is a continuation of application No. 13/140,202, filed as application No. PCT/GB2008/051218 on Dec. 19, 2008, now Pat. No. 8,836,598.

(51) Int. Cl.

| | |
|---|---|
| *H01Q 3/00* | (2006.01) |
| *H01Q 3/04* | (2006.01) |
| *A61B 5/01* | (2006.01) |
| *A61B 5/05* | (2006.01) |
| *G01K 11/00* | (2006.01) |

(Continued)

(52) U.S. Cl.
CPC *H01Q 3/04* (2013.01); *A61B 5/015* (2013.01); *A61B 5/0507* (2013.01); *G01K 11/006* (2013.01); *H01Q 3/14* (2013.01); *H01Q 19/062* (2013.01)

(58) Field of Classification Search
CPC .... A61B 5/015; A61B 5/0507; G01K 11/006; H01Q 19/062; H01Q 3/04; H01Q 3/14
USPC ........................................................ 343/762
See application file for complete search history.

(56) References Cited

U.S. PATENT DOCUMENTS

| | | | |
|---|---|---|---|
| 5,933,120 A | 8/1999 | Manasson et al. | |
| 6,217,210 B1 | 4/2001 | Roeder et al. | |

(Continued)

FOREIGN PATENT DOCUMENTS

| | | | |
|---|---|---|---|
| UA | 56347 C2 | 5/2003 | |
| UA | 85932 C2 | 6/2007 | |

OTHER PUBLICATIONS

International Preliminary Report on Patentability, PCT/GB08/051218, dated Feb. 15, 2011.

(Continued)

*Primary Examiner* — Seung Lee
(74) *Attorney, Agent, or Firm* — Reza Mollaaghababa; Thomas Engellenner; Pepper Hamilton LLP

(57) ABSTRACT

A method of radiometric image generation is provided using a series of isochronous revolutions of a multi-beam antenna with a dispersion characteristic. The antenna is combined with a multi-channel receiver with frequency channel separation to form an imaging unit. The method comprising cyclically executing the following phases: two separate calibration phase; using first and second standards; external radiation reception phase; data processing phase and data transformation phase.

20 Claims, 10 Drawing Sheets

(51) Int. Cl.
*H01Q 3/14* (2006.01)
*H01Q 19/06* (2006.01)

(56) References Cited

U.S. PATENT DOCUMENTS

| | | | |
|---|---|---|---|
| 8,593,157 | B2 | 11/2013 | Adams et al. |
| 8,633,442 | B2 | 1/2014 | Tomioka |
| 9,105,960 | B2 * | 8/2015 | Shylo .................... A61B 5/015 |
| 2007/0046525 | A1 | 3/2007 | Holbrook et al. |
| 2008/0129581 | A1 | 6/2008 | Douglass et al. |
| 2009/0135051 | A1 | 5/2009 | Bishop et al. |
| 2011/0103800 | A1 | 5/2011 | Shinada et al. |
| 2012/0062411 | A1 | 3/2012 | Shylo et al. |
| 2012/0261576 | A1 | 10/2012 | Tomioka |

OTHER PUBLICATIONS

Shilo, S. et al. "Millimeter Wave Imaging System", Physics and Engineering of Microwaves, Millimeter and Submillimeter Waves and Workshop on Terahertz Technologies, The Sixth International Kharkov Symposium on, IEEE, PI, pp. 455-457, XP031129478, ISBN: 978-1-4244-1237-2, Jun. 1, 2007.

Goldsmith P.F., Huguenin G.R., Kapitzky J., Focal Plane Imaging Systems for Millimeter Wavelenghts, IEEE Transactions on Microwave Theory and Techniques, vol. 41, No. 10, pp. 1664-1675, Oct. 1993.

Andrenko S.D., Devyatkov N.D., Shestopalov V.P.—Antenna Array of Millimeter Waves, Doklady Akademii Nauk USSR (Proceedings of the Academy of Sciences of USSR), v. 240, No. 6, pp. 1340-1343, 1978.

Shestopalov V.P., Andrenko SD., Belyaev V.G., Sidorenko Yu.B., Provaiov S.A. "Millimeter and Submillimeter and Submillimeter Surface Electromagnetic Waves Transformation Into Volume Waves and This Phenomenon Utilization in Physics and Technique", The Buiietin of Ukrainian Academy of Sciences No. 1, Sichen, 1977-S. 8-21.

Spravochnik Po Matematike Dlya Ingenerov I Uchaschikhsya VTUZov. Bronshteny I.N., Sernendyayev K.A., M.:Nauka, (Handbook in Mathematics for Engineers and Students. Large Volume in 704 pages) 1981, pp. 233-234.

Hersman M.S., Poe G.A. "Sensitivity of the Total Power Radiometer with Periodical Absolute Calibration", IEEE Transactions on Microwave Theory and Techniques, vol. 29, No. 1, pp. 32-40, 1991.

Buduris J., Chanavie P. "Ultra-High Frequency Chains (Theory and Application)." Translation from French/Editor A.L., Zinovieva.—M. :Sov. Radio, 1979—288 pp. 129-130.

Andrenko S.D., Evdokimov A.P., Kryzhanovskiy V.V., Provalov S.A., Sidorenko Yu B., Skaniruyuschaya Antenna Samoletnogo Radiometricheskogo Kompleksa ("Scanning Antenna of the Aircraft Radio Physical Complex"), Radiofizicheskiye Metody I Sredstva Dlya Issledovaniyaokruzhauyschey Sredy V Millmetrovom Diapazone.: Sb.nauch. tr.—Kiev; Nauk. dumka, pp. 154-160, 1988.

Kuhling H. Physics. Directory, Translation from German / Under Editorship of E.M. Leykin.—M.; Mir. 1980,—4 pages.

Yevdokymov, Anatoliy P. et al. "The Scanning Antenna for a 3-MM Multichannel Radiometer", International Conference on Antenna Theory and Techniques, Sep. 9-12, 2003, pp. 307-309.

* cited by examiner

METHOD FOR FORMATION OF RADIOMETRIC IMAGES AND AN ANTENNA FOR IMPLEMENTATION OF THE METHOD

RELATED APPLICATIONS

The present application claims priority as a continuation application to a patent application entitled "Method For Formation of Radiometric Images And An Antenna For Implementation Of The Method", U.S. patent application Ser. No. 14/457,974, filed Aug. 12, 2014, which is a Continuation of U.S. application Ser. No. 13/140,202, filed Aug. 25, 2011, now U.S. Pat. No. 8,836,598, Issued Sep. 16, 2014, which is a U.S. National Stage of PCT/GB2008/051218, filed Dec. 19, 2008, of which are herein incorporated by reference in their entirety.

The invention refers to passive ultra-high frequency radiowave imaging devices and has been designed for quick formation of radio-thermal images of objects. The method and its implementing antenna can be used, in particular, for formation of radio-thermal images of human body for the purposes of thermometric medical diagnosis, or in the process of customs inspection with the purpose of revealing various objects that may be hidden on human body under clothing.

Presently ultra-high frequency radiometric methods, based on the dependence of the intensity of own radio-thermal radiation of the objects on their physical and chemical parameters, have become widely popular for remote sensing of various media. One of the primary tasks during ultra-high frequency (UHF) radiometric observations is to measure and register the spatial distribution of the intensity of radio-thermal radiation emitted by the object, which is characterized by its brightness temperature $T_b$. In many cases the data concerning, spatial distribution of brightness temperature for objects under investigation can be best represented by two-dimensional radio-thermal images, thereat, the two coordinates of the image correspond to spatial coordinates of the observation field, and brightness or hue of the unitary element of the image characterize the intensity of radio-thermal radiation in accordance with the established scale of brightness temperatures. At that, the higher is radiometric accuracy and spatial resolution capability of the radiometric system while generating radio-thermal images, or in other words, the higher is reproduction accuracy of spatial inhomogenuities (relief) of measured radio-thermal fields, the higher will be the efficiency of using the generated radio-thermal images for various applications, among which, in particular, are the following:

concurrent detection of weapons and smuggled goods on human body under clothing, as well as on vehicles and on guarded objects;

possibility of in-flight generation (onboard the flight vehicle) of high-contrast images of landing runway in complicated weather conditions for provision of secure landing; generation of in-flight warnings to prevent possible collisions with large obstacles (mountains, houses) in case of lack of direct vision;

possibility of generation of high-contrast images of wild fire and landscape fire hot spots from the board of flight vehicle in the conditions of acute fumigation, to provide for navigation and guidance of fire-fighting systems, both on the ground, as well as aerial firefighters (airtankers);

problems of noncontact medical thermometric diagnosis of inflammatory processes during various diseases (on the surface of the body and in subcutaneous layer of biological tissues, or under medical bandages or gypsum layers).

The advantages of millimeter-wave radio imaging systems are high spatial resolution, combined with relatively small dimension of reception antennas, lack of electromagnetic emissions, which may negatively influence the personnel and other people, lack of dependence of the response signal intensity from distance, in the mean time, present technical limitations do not allow full implementation of all potential capabilities of such systems. Among such limitations are complexity and high cost of the system, relatively small observation angles and slowness of image generation which, in certain cases, are insufficient for resolution of above mentioned problems.

A series of technical solutions are known for SHF radiometric systems (see for example, Goldsmith P. P., Huguenin G. R., Kapitzky J. Focal Plane Imaging Systems for Millimeter Wavelengths//IEEE Transactions on Microwave Theory and Techniques, v. MTT-41 No. 10, October 1985, pp. 1864-1675), for which the established observation field is periodically scanned during generation of images:

either by singular needle-shaped beam of the directional pattern of the receiving antenna (DPA) when it is controlled by two spatial coordinates (scanning);

or with the help of multiple-beam DPA which is formed by beam-forming matrices of receivers situated in the focal plane of receiver lens antenna;

The disadvantages of singular beam DPA image generation scheme are the following:

in the case, when the time allotted for generation of full image is limited, —insufficient observation time period of unitary picture element and related potentially low achievable radiometric sensitivity and radio-thermal contrast accuracy values; strict requirements to the velocity parameters of the antenna control device of the radiometric system;

in the case, when high accuracy of restoration of radio-thermal relief is required on the field of observation, significant time interval, required for generation of the image.

Shortcomings of systems with beam-forming matrices in SHF band include the complexity of placing a large number of exciters (measurement channels) in the focal plane of the antenna when dimensions of unitary exciter are physically limited, problems related to construction of beam-forming matrices with spatially solid overlapping beams during construction of highly directed antennae, as well as the high total cost of the systems, related to the square law increase of the number of receiving channel depending on $N^2$ the number of picture elements N on each coordinate. Thereat, each of the mentioned channels should contain a full set of elements common to ultra-high frequency radio-thermal radiation receivers. There are also other methods for generation of radio-thermal images, which combine characteristics of the beam-forming matrices method with the principles of serial spatial retargeting of the group DPA created by the beam-forming matrix, in this case the number of receivers in the system can foe reduced to a technically end economically acceptable figure, but other technical issues would appear, particularly related to the need of fast retargeting group DPA positions in the sector of observation angles.

One of the perspective methods for generation of radio-thermal images in radiowave imaging systems is through the use of scanning antennae based on the effects of transformation of volume waves into surface waves in open electrodynamic structures, which were first researched over 30 years ago (Andrenko S. D., Devyatkov N. D., Shestopalov V. P.—Antenna array of millimeter range//Doklady Akademii nauk USSR, 1978, v. 240, No 6.—P. 1340-1343, Shestopalov V. P., Andrenko S. D., Belyaev V. G., Sidorenko Yu. B., Provalov S. A. Peretvorennya milimetrovikh i submilimetrovikh poverkhnevikh elekromagnitnikh khvil v obyemni i vikoristannya cyogo yavischa u fizici i tekhnici//Naukovi oglyadi i povidomlennya, Visnik A N Ukrainskoy R S R, No 1 Sichen, 1977—S. 8-21). Such antennae usually contain a linear or planar dielectric waveguide, a scattering diffraction grating, placed in its direct proximity, as well as elements to provide concentration of electromagnetic energy and its transmission to the input of radiometric receiver.

There are known systems and methods, for example as disclosed in U.S. Pat. No. 5,933,120, for generation of images based on diffraction gratings including among their primary elements a spindle arrangement to define the axis of rotation, a waveguide arrangement linked to the spindle arrangement and containing the first linear dielectric waveguide, defining the first axis perpendicular to the rotation axis, diffraction grating arrangement, containing numerous sectors, and each sector from the mentioned array contains a different in its period conducting diffraction grating, thereat, the changing period of the diffraction grating is a function of angle set out while rotating the grating point to the rotation axis, and grating plane is perpendicular to the rotation axis. At that this system and the method provide advantages, the essence of which is that the image may be quickly generated with the help of inexpensive radiometric system.

Among the advantages of mentioned systems and methods of their implementation is the possibility for generation of two-dimensional radio-thermal images through one single receiver, through provision of radial movement of the beam from center to the circumference of cone-shaped sector of observation angles, which is achieved by isochronous unidirectional circular movement of the control elements of the antenna. Thereat sign-variable momentums of inertia are eliminated and, as a result, the speed of image generation is increasing, reaching dozens of images per second.

In the mean time, significant disadvantages are inherent to the mentioned systems and methods of implementation.

The first disadvantage is the need of simultaneous rotation, with different velocities, of both dielectric waveguide arrangement with the receiver element and the disc-shaped diffraction grating. Rotation velocity of the dielectric waveguide arrangement defines the image generation speed; rotation velocity of the grating defines the radial component of the speed of movement of the beam in space. Thereat rotation speed of the grating significantly exceeds rotation speed of the dielectric waveguide arrangement and, with high spatial resolution of the antenna, may reach several tens of thousands revolutions per minute. Although such revolution speeds can be achieved technically, this makes the device significantly complicated. The dimensions of s grating unit, which are quite large, define the dimensions of the receiving aperture of the antenna and spatial resolution of the radiowave imaging system. While rotating at high-speed. In essence, it turns into a gyroscopic device which strives to maintain its orientation in the space and thus, on the account of emerging significant mechanical momentums, preventing the change of this spatial orientation, that is, changing the position of the antenna while reviewing the space. Therefore such systems of image generation can be used, first of all, for construction of images while maintaining a stationary spatial position of the sector of observation angles. In order to suppress higher types of electromagnetic oscillations in dielectric waveguides the dimensions of its cross-section should be consistent with the length of received waves. In millimeter range if constitutes just a few millimeters, which results in significant flexibility of the waveguide. While the grating and waveguide are moving relative to each other, provision of permanently fixed distance (gap) between them is one technical problem. This gap is known to define the basic energy parameters of the electrodynamic system of the antenna—the transformation coefficient of spatial electromagnetic wave into surface wave of dielectric waveguide. These peculiarities make difficulties in technical implementation and increase the cost of the device on the account of complex construction of the waveguide arrangement, higher precision requirements of the assembly, complexities of the alignment process of the elements.

The second disadvantage is the necessity of simultaneous rotation, in a single construction, not only the linear dielectric waveguide but also the cylindrical dielectric lens above the waveguide, which focuses downward radiation along the focal line coinciding with the axis of dielectric waveguide. Aperture angle of the antenna in the plane coinciding with the cross-section of the waveguide is established by the dimensions of the lens. At comparable measurements of the diffraction grating and the lens the latter, having finite focal distance, should be located on a significant distance from the dielectric waveguide. The higher is the size of receiver aperture and focal length, the higher will be this distance. This results in a potential increase of the dimensions of the antenna (its depth) and will not allow to implement the declared flat version of the antenna. With short focal lengths the curvature of the lens should be significant, which would result in increased width and mass and, correspondingly, would further increase the rotational momentum of inertia. These peculiarities complicate technical implementation of an antenna system with high operational parameters which, at the same time, should be easy to manufacture and have low cost.

The third disadvantage concerns limitations on the frequency bandwidth of radiation received by the radiometric system, it is known that the <<diffraction grating-dielectric waveguide>> electrodynamic system has expressed angle-frequency dependent properties, about 1° of shifting of the beam per 1% frequency change. During the reception of wideband radiation this results in the expansion of the beam width in the plane corresponding with the longitudinal axis of the waveguide and consequently in reduction of the efficiency of the system—deterioration of spatial resolution and quality of generated images, if the bandwidth of received frequencies is limited by installation of filters on the input of the receiver, this reduces radiometric sensitivity of the system and deteriorates the image quality because of reduced signal/nose ratio. Insufficient sensitivity of the radiometric receiver during singular beam high-speed scanning may lead to significant deterioration of overall image quality because of high noise factor in observation intervals of unitary picture elements. All these peculiarities are limiting the possibilities of implementation of an image generation system with high operational performance.

Fourth disadvantage of the mentioned systems and methods is because of high losses in the antenna and technical difficulties related to implementation of proposed types of diffraction gratings: multiple-sector, multiple-sector with alternating increment, spiral with alternating increment. Their fabrication at reasonable cost may only be possible based on the use of photolithographic methods while using substrates made of dielectric materials. In millimeter range the overwhelming majority of dielectric materials possess high imaginary components of dielectric permeability $\in''$, which results in increase of losses in the antenna and reduction of radiometric sensitivity of the system or, if acceptable sensitivity is attained, ∈" the system lacks required mechanical characteristics (either too brittle, or too flexible) and are too expensive when samples over ten centimeters in diameter with 1 mm thickness are needed. Among such materials are, particularly sapphire and silica glass. Significantly lower radiation losses can be obtained through the use of comb-shaped all-metal diffraction gratings, however fabrication of such gratings with variable curvature profile, or multiple sector gratings, with the required accuracy of profiles, is presently on the verge of possibility from the mechanical perspective. This makes the use of such gratings inefficient because of very high cost. Since active losses in the antenna define, to a significant extent, the overall noise temperature of the system and the attained sensitivity, the abovementioned peculiarities make the implementation of radiometric system of image generation with high technical specifications quite difficult.

At the same time, by utilizing the dispersion properties of such structures, through the use of corresponding procedures for processing of received noise signals, it appears possible to generate multiple-beam direction patterns of the antennas and to control the spatial orientation of these diagrams on the account of synchronous alteration of the parameters of the electrodynamic systems of antennas, providing a field of view in the sector of spatial angles. For example, such scheme of review may be implemented on the basis of reciprocal law of scanning with frame-based principle of image generation (Patent (UA) No 56347), (see FIG. 2), in this case, on the account of division of the overall range of received frequencies into M independent frequency channels (M≥1) and parallel processing of the received by antenna noise signal in each of the M frequency channels, specifically, on the account of sequentially conducted operations of comparing the received radiation with calibrated reference signals, through frequency transformation, amplification, square-law detection, analog-digital conversion, it appears possible to obtain M signals in digital form, the amplitude of which in each given instant of time will correspond, in temperature scale units, to current values of intensity of radio-thermal radiation received by the antenna in each of M frequency bands, and in the same time corresponds to current spatial positions of M beams of the antenna. In case of concordant placement of obtained digital values of intensity of radio-thermal radiation in the cells of two-dimensional data array, in accordance with the number of frequency band M and selected scanning law of the antenna, and conduction of linear or non-linear dimensional change operations on the matrix of these digital values, in accordance with the selected law of space review and required scale of mapping by each of spatial coordinates, under concordant transformation of matrix data values info grades of luminance (hue) in accordance with selected luminance (color) scale, a radio-thermal image may be generated on the display device, reproducing with certain detail the spatial distribution of radio-thermal fields, radiated by the objects situated in the sector of observation angles of the antenna.

The antenna of such multiple beam scanning radiometer may be created on the basis of known engineering solutions, for example, Patent (UA) No 56347, and may contain a planar dielectric waveguide, disk-shaped diffraction grating placed under the dielectric waveguide mounted on the rotational output axis of electromechanical transmission, as well as a parabolic reflector, horn irradiator from planar dielectric waveguide to a hollow metallic waveguide and a disc position sensor, thereat the output of horn irradiator is the output of the antenna, and the input of electromechanical transmission and the output of disc position sensor are the control input and output of the antenna, respectively.

Among the advantages of the method disclosed in Patent UA No 56347 should be listed the possibility of generation of radio-thermal images with presence of only one ultra-high frequency input device in the system, thus significantly reducing its complexity and cost, in comparison with the version containing a beam-forming matrix. The second advantage of the prototype is M times reduction of the beam movement speed and $\sqrt{M}$ times improvement of the sensitivity of the system, in comparison with the singular beam scheme, on the account of concordant M times increase of the signal integration time.

In the same time the reciprocal principle of spatial observation by multiple beam direction pattern of the antenna, utilized in the prototype, has a disadvantage which is expressed in limited speed of image generation. This is related to the use of mechanical motion of disk-shaped diffraction grating with alternating direction in the process of controlling the spatial position of DPA, which takes place in a certain angular sector around the axes oriented near the working surface normal of the dielectric waveguide. For highly directional antennae the cross-dimensions of receiver aperture (diffraction grating) may reach tens of centimeters. Thereby moving elements of the antenna possess a quite high momentum of inertia and maximum attainable observation speeds and refreshing of images may not exceed several Hertz with reciprocal movement of beams. This is insufficient for the systems of operating supervision, where data refreshing speed should exceed 10 images per second.

The second disadvantage of this method is because of limitations of the attainable sector width of observation angles on that coordinate, by which frequency division of the reception directions is performed. The electrodynamic system of the antenna has angle-frequency dependence, which results in certain limitations of working bandwidth because of deteriorating of energy transformation coefficient on the brinks of the band at fixed parameters of the dielectric waveguide and diffraction grating. Thereat efficient transformation of volume electromagnetic waves into surface waves may take place in a limited bandwidth, around ~16 to 20% from the central frequency. At realizable values of angle-frequency coefficient of the antenna about 0.9 to 1 degrees of the beam sweep per 1% frequency change the mentioned bandwidth determines the attainable size of the observation angle sectors by that coordinate with the value around 15° to 20°, which is insufficient for remote sensing and operating supervision of the environment.

Among disadvantages of the antenna in the prototype device is the need to change mutual positions of the diffraction grating and dielectric waveguide in the process of scanning. By turning the diffraction grating the orientation of scattering elements of the grating will change in relation to the phase front of electromagnetic wave propagating in the dielectric waveguide, on which account the parameters of mentioned electrodynamic system will change too, and, as a result, will change the spatial orientation of the antenna beam (beams). At the same time, such variation of the elements of electrodynamic system will also stipulate the change of energy characteristics of the antenna: transformation efficiency of volume electromagnetic wave into surface wave of dielectric waveguide declines with inclination of the beam (beams) from the initial position, at which scattering elements of the grating are oriented in parallel to the phase front of the surface wave of dielectric waveguide. Similarly, inclination of the beam from the initial position corresponding to the initial position of the grating brings to the increase of the width of the beam (beams) of the antenna as a result of effective dimensions of the receiver aperture in accordance with the change of aperture's projection on viewing direction; that is, inclination of the beam results in the reduction of antenna area utilization coefficient of the antenna. Thus, for the mentioned method of radiometric images generation energy-transfer factor of the antenna and beam width are functions of the scanning angle, which prohibits the attainment of equally high DPA parameters in the whole sector of observation angles, and therefore it is not possible to attain same image quality on the whole field; this potentially results in deterioration of quality of generated images.

Another disadvantage of the prototype antenna is related to technological complexities in the process of its fabrication and alignment. Since in the process of operation the diffraction grating and planar dielectric waveguide should be positioned on a certain calibrated distance, which is selected in the process of alignment of the antenna and should remain invariable in the process of scanning, construction of the antenna should satisfy these conditions. As a result, the requirements to mechanical characteristics of the elements—flat surface accuracy of the diffraction grating and planar waveguide, are quite high—which is a limiting factor for the types of applicable dielectric materials. For example, a planar waveguide made of polystyrene, which possesses quite high rigidity and stability of mechanical characteristics, is unsuitable in a millimeter range applications because of about twice higher losses in comparison with, for example, PTFE; PTFE, however, cannot be used without reservations in such construction because of its cold flow and instability of mechanical characteristics at exploitation period. Since rotation of the diffraction grating respective to dielectric waveguide is one of the key features of the mentioned method of image generation and thus defines the construction and mechanical characteristics for the material of dielectric waveguide, the mentioned features are among disadvantages of the antenna, reducing its attainable technical parameters, increasing its complexity and cost.

The essence of the first invention of the group is to improve the method of radiometric images generation on the account of transition from group reciprocal linear movement to isochronous circular movement of multiple-beam direction patterns of the antenna, thus-providing an improvement, of maximum speed of image generation, improvement of radiometric resolution in central part of the image and expansion of the sector of observation angles.

The essence of the second invention of the group is to improve the scanning multiple-beam antenna on the account of transition to circular principle of scanning, thus providing an increase of scanning speed, reduction of active losses, improvement of aperture area utilization coefficient, attainment of better technological effectiveness and reduction of manufacturing costs.

The first issue is resolved on account of the fact that, in the method of radiometric images generation, based on cyclical repeating of an algorithm, consisted of the procedures of measurement and processing of data, executed with the use of four basic time intervals, named as the calibration phase by first standard with $\Delta t_{cs1}$ duration, calibration phase by second standard with $\Delta t_{cs2}$ duration, external radiation reception phase with $\Delta t_{ex}$ duration, and data processing phase with $\Delta t_{pr}$ duration, at that, data processing phase $\Delta t_{pr}$ follows after the external radiation reception phase $\Delta t_{ex}$, and calibration phases $\Delta t_{cs1}$ and $\Delta t_{cs2}$ which may be executed in any order, precede the external radiation reception phase $\Delta t_{ex}$, at that, reception of external radio-thermal radiation takes place during the external radiation reception phase $\Delta t_{ex}$ from a two-dimensional sector of angles represented in an orthogonal coordinate basis and characterized by independent coordinates $\Theta$ and $\Phi$, calculated from a spatial vector defining the antenna aperture plane and by angular sector $\Delta\Theta=(\Theta_{fin}-\Theta_{ini})$ of the $\Theta$ coordinate, with coordinates of the initial and final observation angles $\Theta_{ini}$ and $\Theta_{fin}$, respectively, as well as M (M≥1) independent observation directions with spatial orientation $\theta_m$ (M≥m≥1) along mentioned spatial $\Theta$ coordinate. M values of the radio-thermal radiation intensity $E_{i,m}$, simultaneously received by M beams of the antenna. These M values are processed in M reception channels concurrently and in accordance with a unified measurement procedure and are then transformed into a one-dimensional array of digital values $[C_m]$ during the calibration phase by first calibration standard $\Delta t_{cs1}$ simultaneously M reception channels receive the first calibration radiation with known or calculated intensity $T_{c1,m}$ in units of temperature scale, and the received signals are processed concurrently and in accordance with a unified measurement procedure in M reception channels and are transformed into a one-dimensional array of digital values $[C_{c1,m}]$ with dimensionality [M], during the calibration phase by second calibration standard $\Delta t_{cs2}$ simultaneously M reception channels receive the second calibration radiation with known or calculated intensity $T_{c2,m}$ in temperature scale units, and received signals concurrently and in accordance with unified measurement procedure are processed in M reception channels and transformed into a one-dimensional array of digital values $[C_{c2,m}]$ with number of dimensions [M], during the processing phase $\Delta t_{pr}$ the received arrays of digital data $[C_m]$, $[C_{c1,m}]$, $[C_{c2,m}]$, $[T_{c1,m}]$, $[T_{c2,m}]$ are processed simultaneously in accordance with the data processing procedure for calculation of radio-brightness temperatures of received radiation, as a result of which is formed a one-dimensional array of values with number of dimensions [M], the values $[T_{b,m}]$ of which, represented in units of the temperature scale characterize distribution of intensity of radio-thermal radiation $E_{i,m,n}$ for one independent direction of observation n (N≥n≥1) from N (N≥1) observation directions along a different from $\Theta$ direction independent spatial coordinate, at that, in addition to the above, $\theta_m$ directions simultaneously arise in a dispersive antenna with of radiometric system on the account of frequency division of reception directions on spatial coordinate $\Theta$ on M independent directions by splitting the general bandwidth of the radiometric system $\Delta f$ into M narrower bandwidths $\Delta f_m$, each of which characterizes a separate receiving channel number m with total number of these channels M, at that the procedure of measurement in each of M receiving channels includes consecutive operations of filtration and amplification of signals in ultra-high frequency range in general for all channels bandwidth $\Delta f=(f_{ini}-f_{fin})$, where $f_{ini}$ and $f_{fin}$, are, respectively, the initial and final values of radiation frequency received by radiometric system in ultra-high frequency (UHF) range, segregation of the signal in frequency band $\Delta f_m=(f_{m,ini}-f_{m,fin})$, where $f_{m,ini}$ and $f_{m,fin}$, respectively, are the initial and final values of frequency of received radiation in channel with number m attributed to the range of ultra-high frequencies, at that the mentioned values $f_{m,ini}$ and $f_{m,fin}$ successively change from channel to channel and are selected so that, along with bands $\Delta f_m$ in M reception channels without omissions covers the whole frequency band $\Delta f$, and $\theta_m$ directions corresponding to bands $\Delta f_m$ concordantly and without omissions cover the whole sector of angles $\Delta\Theta$, and, finally, successively executed in each channel operations of square-law detection, integration, analog-digital conversion and digital accumulation and besides, the procedure of data processing includes consecutively executed operations of calculating for each of m reception channels the $S_m=(T_{c1,m}-T_{c2,m})/(C_{c1,m}-C_{c2,m})$ coefficients, defining the values of steepness of linear dependence of transformation of output digital values $C_m$ into the values of external radiation radio-brightness temperatures $T_{b,m}$, and then calculations of $T_{b,m}$ values according to found linear dependences proportionally as $T_{b,m}=S_m \cdot (C_m-C_{c2,m})+T_{c2,m}$ with a following formation of a two-dimensional array $[T_{b,m,n}]$ with number of dimensions [dimensionality] [M×N] for M·N independent observation directions by both independent coordinates of the image, in accordance with the invention formation of images takes place with simultaneous isochronous circular movement of M beams of the antenna and is implemented on the account of turning the receiver aperture of the antenna around a spatial axis defining the main observation direction with coordinates $[\Theta_{main}, \Phi_{main}]$ during the revolution period $T_{rev}$ by angle $\Psi=360°$ with simultaneous synchronous revolution of mentioned coordinate system around same spatial axis to the same angle $\Psi=360°$ with simultaneous representation of image coordinates in coordinate system $(\Theta, \Psi)$ and introduction of file initial $\Psi_{ini}$ and final $\Psi_{fin}$ values of observation angles by $\Psi$ coordinate, defining the sector of observation angles $\Delta\Psi=(\Psi_{fin}-\Psi_{ini})$ by $\Psi$ coordinate while splitting this sector into N (N≥1) independent observation positions $\Psi_n$ (N≥n≥1) along $\Psi$ coordinate and introduction of the fifth basic time interval into the algorithm which is a part of the data processing procedure and named coordinate transformation phase with the duration $\Delta t_{ctr}$ during which the procedure of transformation of spatial coordinates of the picture elements from coordinate system $(\Theta,\Psi)$ into reference frame $(\Theta,\Phi)$ is performed for the generated two-dimensional array of values of radio-brightness temperatures $[T_{b,m,n}]$, at that the main observation direction $\Theta_{main}$ by coordinate $\Theta$ takes any values in the sector of angles from 0° to 90°, and by coordinate $\Phi$ the main observation direction $\Theta_{main}$ takes zero value ($\Phi_{main}=0$), besides, certain phases can be executed multiple times in various combinations depending on the selected duration of execution of calibration phases by the first calibration standard $\Delta t_{cs1}$, calibration by the second calibration standard $\Delta t_{cs2}$, reception of external radiation $\Delta t_{ex}$ in reference to revolution period $T_{rev}$, specifically, reception phase of external radiation $\Delta t_{ex}$ can be executed P times consecutively (P≥1), thus forming an accumulation cycle with duration $\Delta t_{ac}$, when P=1 the algorithm contains a group of consecutively executed calibration phase by first calibration standard $\Delta t_{cs1}$, calibration phase by second calibration standard $\Delta t_{cs2}$, reception phase of external radiation $\Delta t_{ex}$ and processing phase $\Delta t_{pr}$, repeating the mentioned group I consecutive times (I≥1), after which the coordinate transformation phase $\Delta t_{tr}$ is executed, and when P>1 the algorithm consists of consecutively executed calibration phase by the first calibration standard $\Delta t_{cs1}$ and calibration phase by the second calibration standard $\Delta t_{cs2}$, after which repeatedly J times consecutively (J≥1) the group consisting of consecutively executed accumulation cycle $\Delta t_{ac}$, processing phase $\Delta t_{pr}$ and coordinate transformation phase $\Delta t_{tr}$, is executed, besides, data accumulation takes place with accumulation interval $\tau_m \leq \Delta t_{ex}/N$ during the reception phase of external radiation $\Delta t_{ex}$ with concordant increase of the accumulation interval $\tau_m$ in accordance with proximity of spatial coordinates $\theta_m$ to the main observation direction $[\Theta_{main}]$, with accumulation interval $\tau_{c1m} \leq \Delta t_{cs1}$ during the calibration phase $\Delta t_{cs1}$ by first calibration standard and with accumulation interval $\tau_{c2m} \leq \Delta t_{cs2}$ during calibration phase $\Delta t_{cs2}$ by second calibration standard.

Such modification of the method of radiometric images generation allows to improve the speed of image generation, increase radiometric resolution in central part of the images, located near the main observation direction, extend the sector of observation angles while maintaining the number of processing channels M and frequency band $\Delta f$ on the account of meeting the following conditions.

1) With isochronous unidirectional circular motion of the antenna, in absence of sign-variable mechanical momentums, significantly higher image generation speeds are attainable, compared with reciprocal linear movement of the internal elements of the antenna.

2) With rotational motion of the antenna's direction patterns its U beams are moving with equal angular speeds but with different linear speeds, at that, the number of independent picture elements (pixels), positioned along the circular trajectory of the beam changes proportionally with the increase of radius (length of trajectory). Thus temporal integration intervals $\tau_m$ in channels of a radiometric system may be selected concordantly with linear velocity of beam propagation, at that, the closer is the beam to the center, the longer integration time may be attained; for example, for a beam the orientation of which is the same as main direction of observation (rotational axis of the antenna), there is no linear motion and its integration interval may be equal to scanning period, or $N \cdot \Delta t_{ex}$. On this account radiometric resolution (fluctuation sensitivity) increases for the central part of the image and, as a result, image qualify improves, 3) With circular scanning the sector of observation angles is twice the value of observation angles difference for outermost beams $\theta_1$ and $\theta_M$ of the direction pattern which, at invariable frequency band $\Delta f$ and invariable number of processing channels M doubles the dimensions of the sector of observation angles in comparison with linear reciprocal movement. At the same time, if keeping high efficiency of the antenna on transformation of electromagnetic volume waves into surface waves in the whole sector of observation angles.

The second stated problem is resolved by the provision of an antenna containing a planar dielectric waveguide and a two-dimensional diffraction grating, irradiator, electromechanical transmission and a position sensor. The planar dielectric waveguide and the two-dimensional diffraction grating are associated by a diffraction field. The receiving aperture plane is positioned closest to the received radiation side of planar dielectric waveguide. The input of the irradiator is connected to the output of planar dielectric waveguide. The input of electromechanical transmission and output of the position pickup sensor are, respectively, the control input and control output of the antenna, in addition a pedestal unit, rotating waveguide transition and a rotating force canceller has been added. The electromechanical transmission, rotating force canceller, position sensor and rotating waveguide transition are mounted on the pedestal unit. The output shaft of electromechanical transmission, the rotating force canceller and the rotating waveguide transition are coaxial with the possibility of rotation around the common axis. The rotating force canceller, through a kinematic scheme, is linked to the output shaft of electromechanical transmission. The planar dielectric waveguide, two-dimensional diffraction grating and irradiator are mechanically rigidly bound with each other and form an integrated constructional assembly; which is named antenna rotor. The antenna rotor is mechanically rigidly bound with the output shaft of electromechanical transmission. The output of the irradiator is connected to the rotating input of the rotating waveguide transition, the immobile output of which is the output of the antenna.

This engineering solution allows an improvement in the speed of image generation, an increase in the radiometric resolution in central part of the images in the vicinity of the main observation direction, an increase in the scanning velocity, aperture area utilization ratio and ease of manufacture, and an expansion in the sector of observation angles without changing the number of processing channels M and invariable frequency band $\Delta f$. This solution is realized through the following criteria;

1) With isochronous unidirectional circular motion of the antenna, in absence of sign-variable mechanical momentums, significantly higher image generation speeds are attainable, compared with reciprocal linear movement of the internal elements of the antenna.
2) While turning the whole antenna assembly during the scanning the width of beams $\Delta\phi_m$ of the directional pattern of antenna in coordinate plane $\Phi$, which is orthogonal to coordinate plane $\Theta$, remains invariable, since during the scanning phase there are no internal changes in the antenna. Since at that, all M beams of the antenna by coordinate $\Phi$ are oriented perpendicularly to the aperture plane, potentially best angular resolution $\Delta\phi_m$ is realized for each of the beams, thus improving the area utilization ratio of the antenna aperture.
3) Two-dimensional diffraction grating and planar dielectric waveguide of the antenna may be implemented as an integrated constructional assembly with invariable position of elements, which simplifies the assembly and alignment of the antenna and allows to provide for flat surface accuracy condition dielectric waveguide since, through the use of intermediate structural components (for example, gaskets made of dielectric material) it may recline against mechanically more rigid diffraction grating. Both these elements may be fabricated as a single unit, made of double-sided foil-clad dielectric, while the diffraction grating is deposited on one of the metallic surfaces by photo-lithographic method. Mentioned peculiarities improve production effectiveness during mass production, reduce the cost of elements and the expenses for the alignment of the antenna. Requirements to mechanical characteristics of dielectric material are significantly relaxed, and it is possible to choose the material with least losses in millimeter range of waves. At that, it is possible to reduce the losses in the antenna and its cost.

According to the present invention there is provided a method of radiometric image generation using a series of isochronous revolutions of a multi-beam antenna with a dispersion characteristic, wherein the antenna is combined with a multi-channel receiver with frequency channel separation to form an imaging unit, the method comprising cyclically executing the following phases: two separate calibration phases $\Delta t_{cs1}$, $\Delta t_{cs2}$ using first and second standards; external radiation reception phased $\Delta t_{ex}$, data processing phase $\Delta t_{pr}$, and data transformation phase $\Delta t_{tr}$. During each revolution of the antenna, one or two full images are generated using this method. The reception phase of the external radiation $\Delta t_{ex}$ may be executed consecutively P (P≥1) times forming an accumulation cycle $\Delta t_{ac}$ with a duration $P\cdot\Delta t_{ex}$. The image is typically a segment of a circle.

The total duration of the calibration phase by the first calibration standard $\Delta t_{cs1}$, the calibration phase by the second calibration standard $\Delta t_{cs2}$, the accumulation cycle $\Delta t_{ac}$, processing phase $\Delta t_{pr}$ and coordinate transformation phase $\Delta t_{tr}$, executed consecutively may be equal to the rotation time period $T_{rev}$ of the antenna.

Alternatively, the total duration of the calibration phase by the first calibration standard $\Delta t_{cs1}$, the calibration phase by the second calibration standard $\Delta t_{cs2}$, the accumulation cycle $\Delta t_{ac}$ executed consecutively may be equal to the rotation time period $T_{rev}$ of the antenna. Alternatively, the consecutively executed calibration phase by the first calibration standard $\Delta t_{cs1}$, calibration phase by the second calibration standard $\Delta t_{cs2}$, reception phase of external radiation $\Delta t_{ex}$ (P=1) and processing phase $\Delta t_{pr}$ may be performed cyclically N times in a row (I=N, where N is number of independent beam positions per revolution), with a total duration of the mentioned cycle of N repetitions equal to the rotation time period $T_{rev}$. In this case, the coordinate transformation phase $\Delta t_{tr}$ is subsequently executed independently. The transformation phase $\Delta t_{tr}$ is preferable performed during the revolution following the revolution during which the data was received.

Alternatively, the total duration of the execution of calibration phases by the first calibration standard $\Delta t_{cs1}$, by the second calibration standard $\Delta t_{cs2}$ and reception of external radiation $\Delta t_{ex}$ is the same for any element of the cycle with a number i (I≥i≥1) and is equal to the $(1/N)^{th}$ part of the rotation period $T_{rev}$, and the processing phase $\Delta t_{pr}$ may be executed independently in the course of regular $(i+1)^{th}$ element of the cycle.

In the course of execution of each regular element of the cycle with a number i (I≥i≥1) each of the calibration phases may foe alternately excluded, and in the course of execution of processing phase $\Delta t_{pr}$ the data is obtained for the (i−1) element of the cycle. In particular, in the course of execution of each regular element of the cycle with a number i (I≥i≥1) one of the two mentioned calibration phases is alternately excluded, either the calibration standard $\Delta t_{cs1}$, or $\Delta t_{cs2}$. In case of exclusion in the element of the cycle under number i, the calibration phases by the first calibration standard $\Delta t_{cs1}$, in the course of execution of processing phase $\Delta t_{pr}$ the mentioned data arrays of values obtained are used for the $(i-1)^{th}$ element of the cycle in the capacity of data arrays of values $[C_{c1,m}]$, $[T_{c1,m}]$, where $[C_{c1,m}]$, are digital outputs of M (M≥1) radiometric channels (1≤m≤M) in the case of receiving the signals from the first calibration standard, $[T_{c1,m}]$ are calibration signals intensity for the first calibration standard with units of temperature. In the case of exclusion in the element of the cycle under the number i the calibration phases by the second calibration standard $\Delta t_{cs2}$, in the course of execution of processing phase $\Delta t_{pr}$ the mentioned data arrays are used in the capacity of the data arrays of the values $[C_{c2,m}]$, $[T_{c2,m}]$, which are obtained for the (i−1) element of the cycle, where $[C_{c2,m}]$, are digital outputs of M radiometric channels in the case of receiving the signals from the second calibration standard, $[T_{c2,m}]$ are calibration signals intensity for the second calibration standard.

The total duration of the consecutively executed calibration phase by the first calibration standard $\Delta t_{cs1}$ and the calibration phase by the second calibration standard $\Delta t_{cs2}$, may be equal to rotation time period $T_{rev}$ and the consecutively executed accumulation cycle $\Delta t_{ac}$, processing phase $\Delta t_{pr}$ and coordinate transformation phase $\Delta t_{tr}$ may be executed cyclically J times in a row (J≥1). In addition the data processing phase $\Delta t_{pr}$ and coordinate transformation phase $\Delta t_{tr}$ may have a total duration which is less than rotation time period $T_{rev}$ and may be executed independently from the calibration phases $\Delta t_{cs1}$, $\Delta t_{cs2}$ and accumulation cycle $\Delta t_{ac}$ within the time limits of the next rotation time period $T_{rev}$.

The values of $[C_{c1,m}]$, $[T_{c1,m}]$, and $[C_{c2,m}]$ $[T_{c2,m}]$ data array elements for the current element of the cycle under number i (I≥i≥1) may be the mean arithmetic values for each element of these data arrays, obtained by utilization of K (K≥1) preceding significant of these elements in K preceding elements of the cycle, counted out from number i.

The capacity of expansion measure for accumulation cycle $\tau_m$ within the time period of external radiation reception $\Delta t_{ex}$, in accordance with the proximity of spatial coordinates $\theta_m$ to the main direction of observation $\Theta_{main}$, the following expression may be used $$\tau_m \leq \frac{\Delta t_{ex} \cdot |\Delta\Theta|}{N \cdot (|\Theta_{main} - \theta_m| + |\Delta\Theta|/M)}.$$

The main direction of observation $\Theta_{main}$ may take one of the two values by $\Theta$ coordinate, respectively either $\Theta_{ini}$ or $\Theta_{fin}$, at that the spatial orientation of the aperture plane of the antenna remains unchanged in time.

The main direction of observation $\Theta_{main}$ may alternatively take any value of the $\Theta$ coordinate, which are within the sector $\Delta\Theta$, with the exception of $\Theta_{ini}$, $\Theta_{fin}$, at that the spatial orientation of the of the aperture plane of the antenna remains unchanged in time.

In either of the above configurations, the spatial orientation of the aperture, plane of the antenna is changed by an arbitrary law.

The main direction of observation $\Theta_{main}$ may take value by $\Theta$ coordinate outside the $\Delta\Theta$ sector, at that the spatial orientation of the aperture plane of the antenna remains unchanged in time, at simultaneous uniform linear movement of antenna in the same plane.

Furthermore, according to the present invention there is provided an antenna comprising an antenna rotor comprising a planar dielectric wave-guide, a two-dimensional diffraction grating and an irradiator and a rotating wave-guide transition configured to rotate relative to the antenna rotor. The planar dielectric wave-guide may be parallel to the diffraction grating. Alternatively or additionally, the planar dielectric wave-guide and the diffraction grating may be provided on a common substrate. In particular, the common substrate may be a dielectric material with a foil coating to provide the diffraction grating. The planar dielectric wave-guide may be non-parallel to the diffraction grating. This configuration provides a better electromagnetic field distribution across the diffraction grating as a result of a reduction in side lobes for this configuration. The largest gap is providing near the irradiator side.

The antenna may further comprise a force canceller configured to rotate relative to the antenna rotor. The antenna may further comprise an electromechanical transmission comprising a motor configured to rotate at least the antenna rotor around an axis in a first direction. The antenna may further comprise a second motor configured to rotate the force canceller in a second direction about the axis, opposite to the first direction. The antenna may further comprise a two-dimensional non-rotating axially symmetric dielectric lens. The lens axis may be coaxial with the axis of the electromechanical transmission.

The antenna may further comprise a sensor configured to measure the angular position of the antenna when if rotates. The sensor may be located within the electromechanical transmission.

The antenna according to the present invention may be combined with a multi-channel radiometric receiver with frequency channel separation in order to provide an imaging unit. The sensor may be further configured to synchronize the data processing means with the angular position of the antenna.

The imaging unit may further comprise, at least one radiation source for calibrating the multi-channel radiometric receiver. The radiation source is configured to provide two distinct reference signals. The first may be created with the active noise radiation source with attenuation of the signal by a directional coupler and the switch in "on" or "off" position. The second radiation reference signal may be the black body radiation of the device with the switch in the "off" position and active noise source in "off" position.

The imaging unit may further comprise a second radiation source for calibrating the multi-channel radiometric receiver. The imaging unit may further comprise means for processing data received by the multi-channel receiver and means for transforming the processed data.

The antenna or the imaging unit may be used to execute the above described method.

The present invention will now be described, by way of example only, with reference to the accompanying drawings in which:

FIG. 1 illustrates the main elements of a radiometric system, illustrating the method of image generation and composition of the scanning antenna;

FIG. 2 schematically illustrates the coordinate grid of radiometric image during multiple-beam reciprocal scanning;

FIG. 3 schematically illustrates the coordinate grid of radiometric image during multiple-beam circular scanning;

Figure 7:
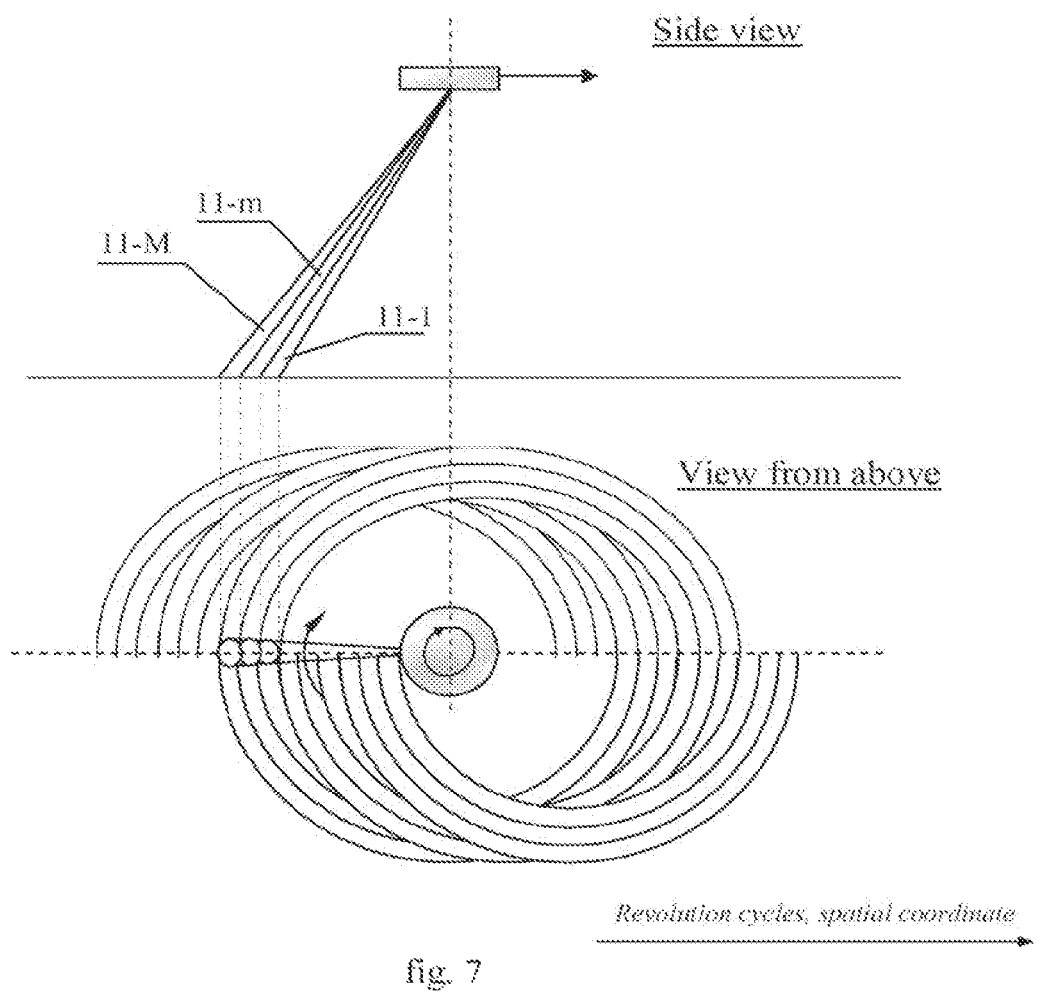
Figure 8A:
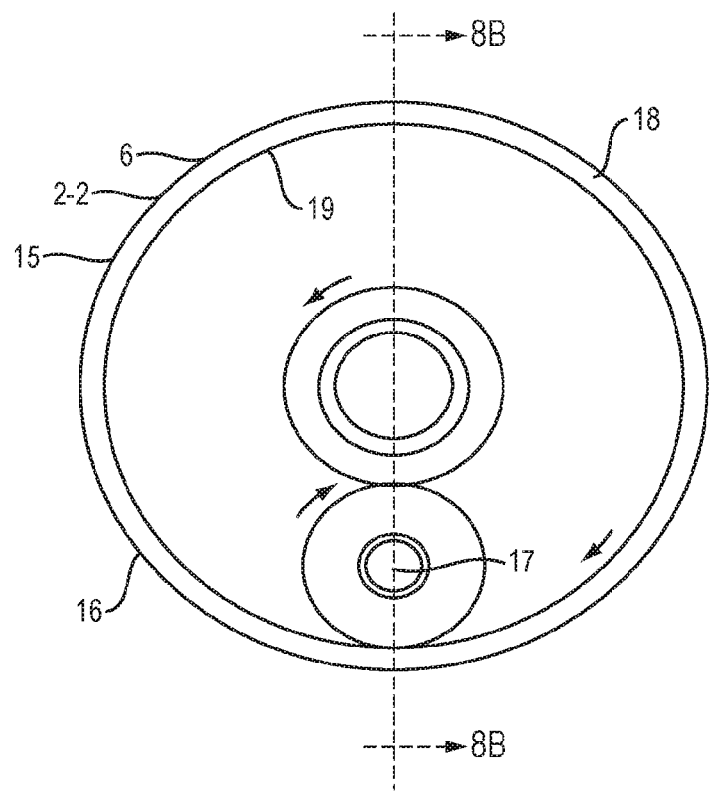
Figure 8B:
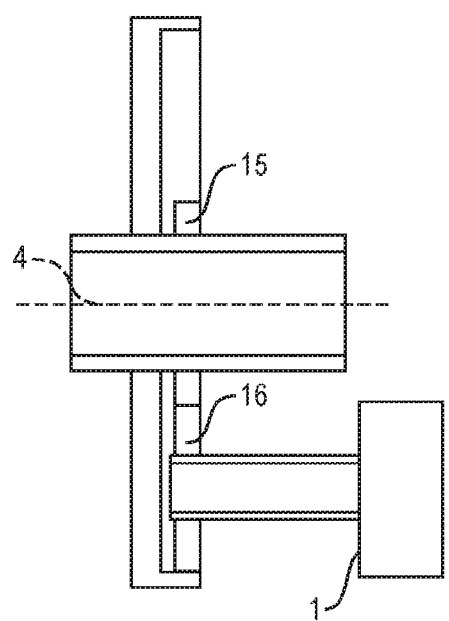
Figure 9:
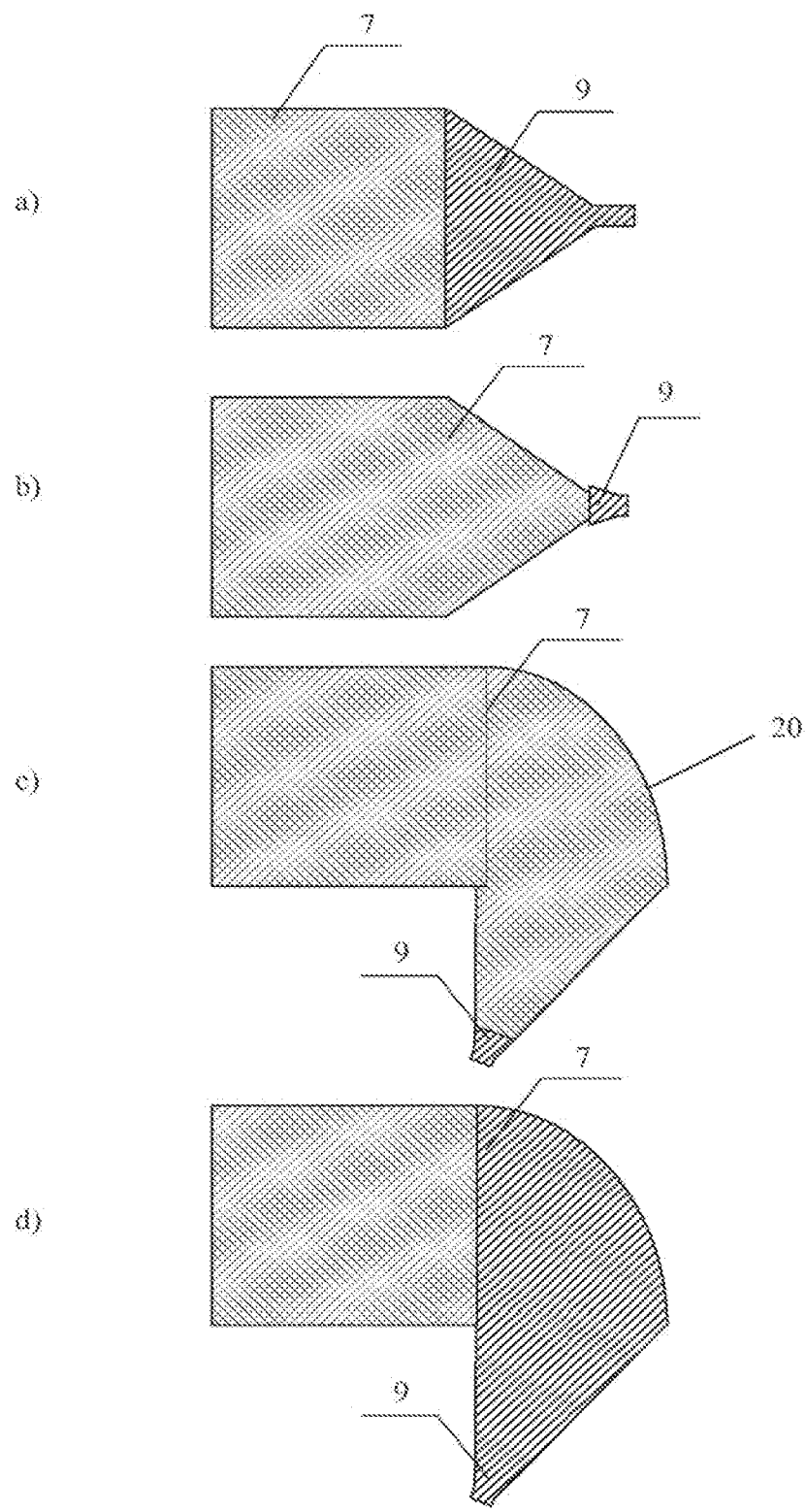
Figure 11:
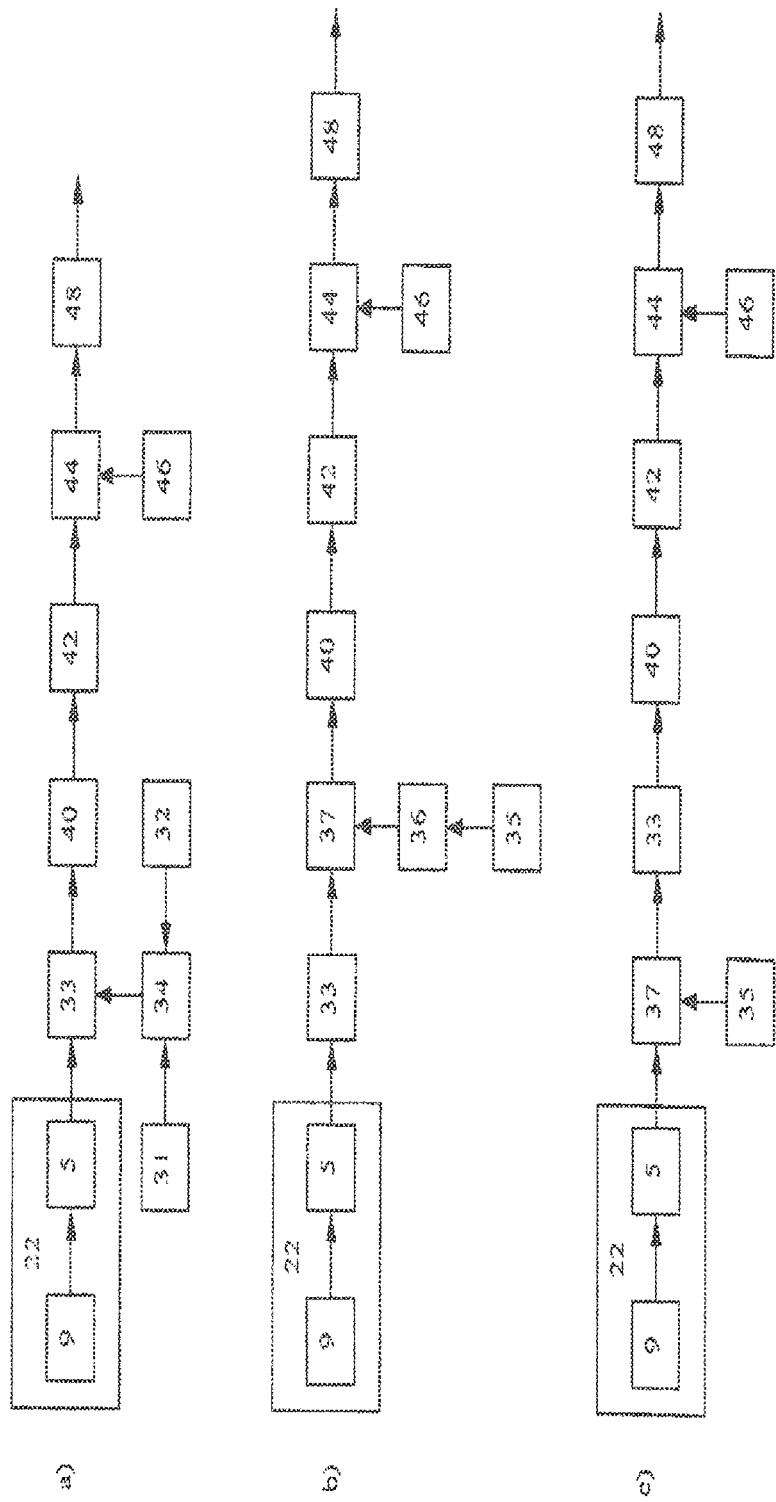
Figure 11:
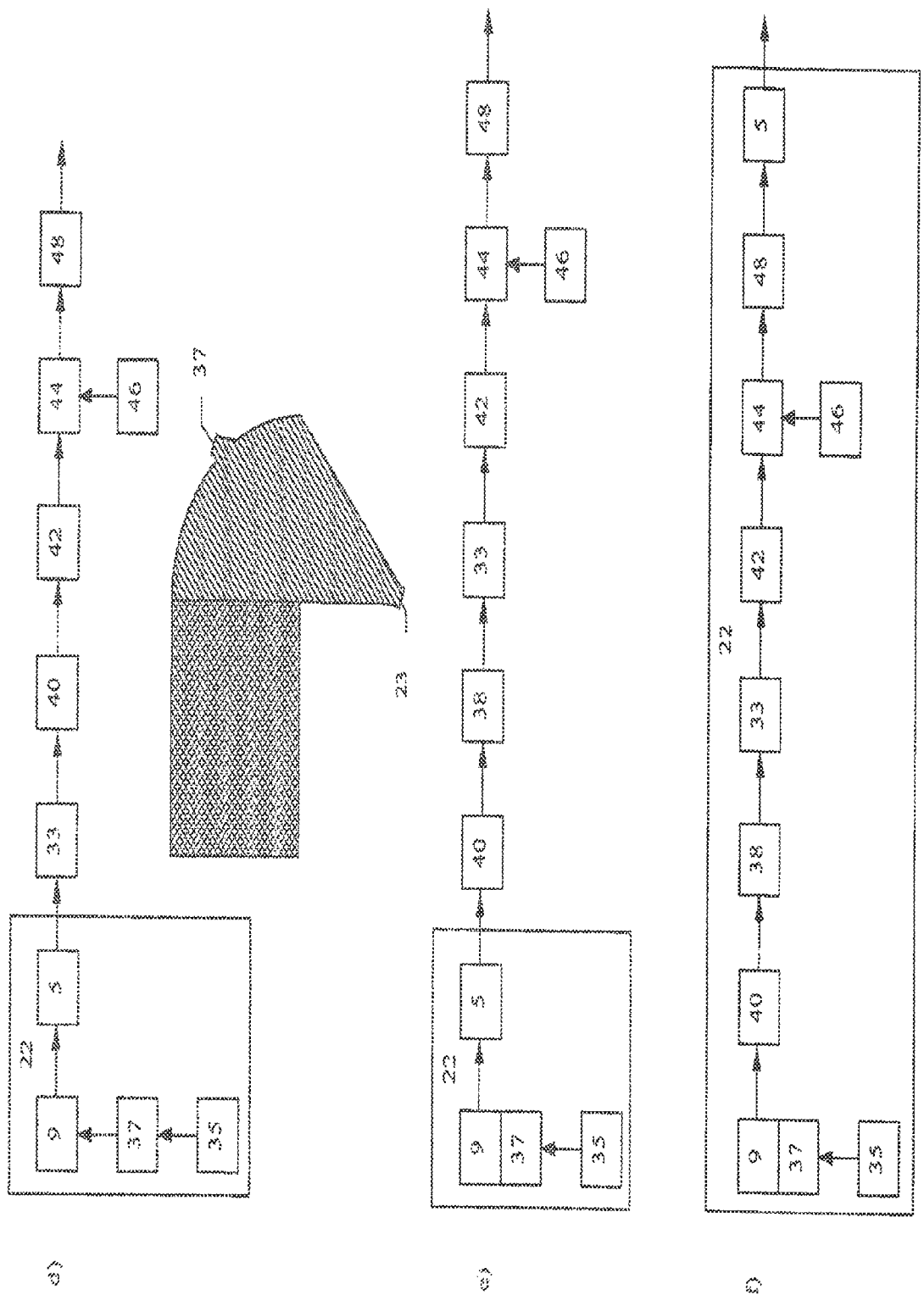

FIG. 7 gives the principle of image generation during isochronous linear propagation of the antenna;

FIG. 8 pictures the structural composition of the angular momentum canceller;

FIG. 9 shows a number of different configurations for the waveguide and the irradiator;

FIG. 10 shows a number of different configurations for the antenna;

FIG. 11 shows a number of different configurations of the imaging unit; and

Figure 12:
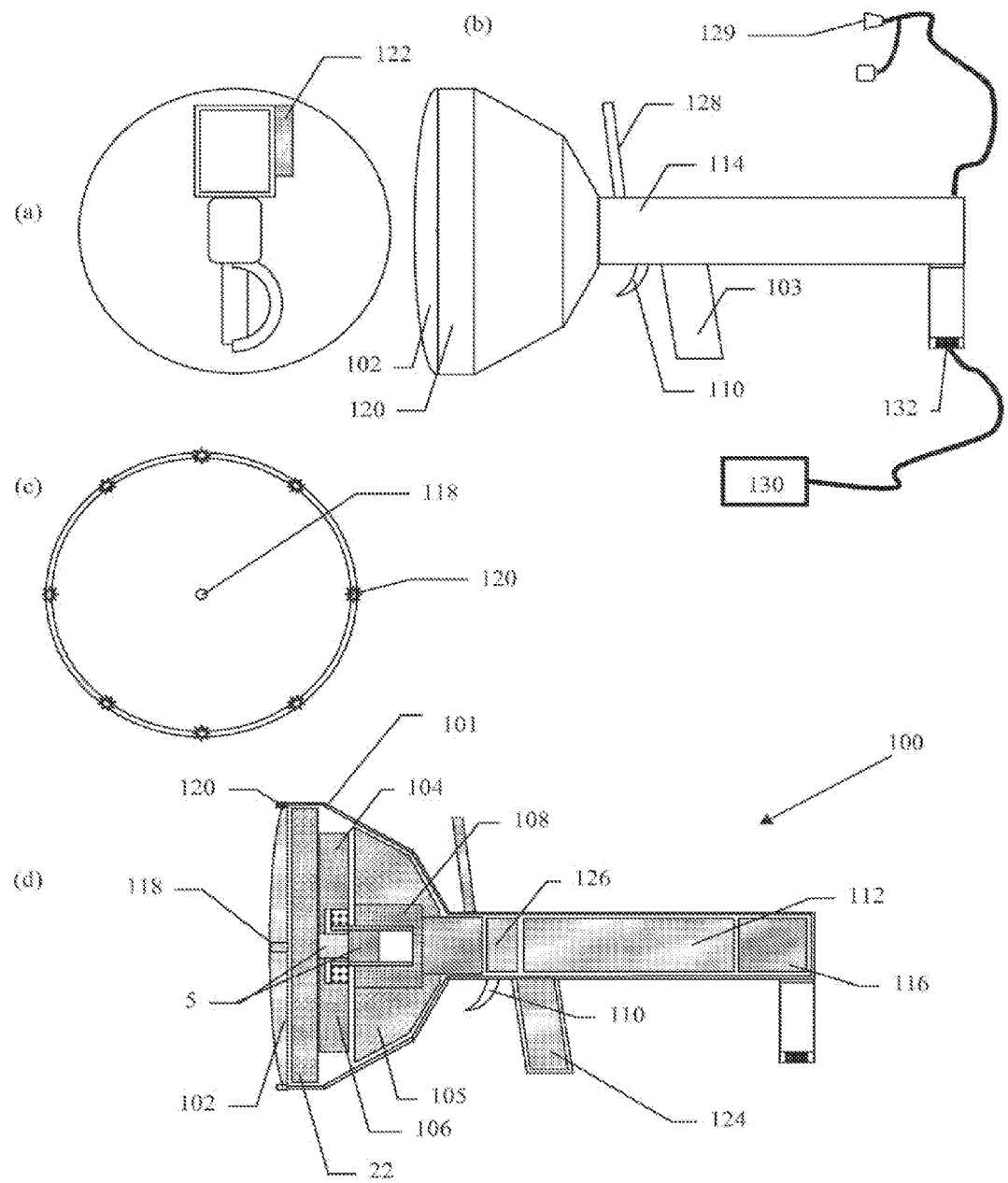

FIG. 12 shows one example of a device incorporating the imaging unit according to the present invention.

Claimed method for generation of radiometric images is implemented in the following way (see, FIG. 1, FIG. 3, FIG. 4, FIG. 6a).

An algorithm comprising of the procedures of measurement and processing of data, cyclically repeated in time and executed during five time intervals named as calibration phase by first standard with $\Delta t_{cs1}$ duration, calibration phase by second standard with $\Delta t_{cs2}$ duration, external radiation reception phase $\Delta t_{ex}$, which may be executed P times consecutively (P≥1), forming an accumulation cycle with $\Delta t_{ac}$ duration, data processing phase with $\Delta t_{pr}$ duration, data transformation phase $\Delta t_{tr}$, at that successively executed data processing phase $\Delta t_{pr}$ and data transformation phase $\Delta t_{tr}$ follow after the accumulation cycle $\Delta t_{ac}$ of P repeated external radiation reception phases $\Delta t_{ex}$, and calibration phases $\Delta t_{cs1}$ and $\Delta t_{cs2}$ which are executed in any sequence, precede the accumulation cycle $\Delta t_{ac}$ of P external radiation reception phases $\Delta t_{ex}$. At that, during any of the P external radiation reception phases $\Delta t_{ex}$ external radio-thermal radiation is received from the environment from two-dimensional sector of angles, which is characterized by orientation of axes of spatial coordinates of the directional pattern of antenna in $\Theta$ and $\Psi$ directions, with coordinates of initial observation angles, respectively, $\Theta_{ini}$ and $\Psi_{ini}$, final observation angles, respectively, $\Theta_{fin}$ and $\Psi_{fin}$, sector sizes, respectively, $\Delta\Theta=(\Theta_{fin}-\Theta_{ini})$ and $\Delta\Psi=(\Psi_{fin}-\Psi_{ini})$, and also M (M≥1) and N (N≥1) independent observation directions, respectively, along each of the mentioned spatial coordinates and with spatial orientation, respectively, $\theta_m$(M≥m≥1) and $\psi_n$(N≥n≥1). For example, values of these parameters may be, by $\Theta$ coordinate; $\Theta_m=2°$, $\Theta_{fin}=16°$ from the normal to the aperture plane of the antenna, $\Delta\Theta=14°$; by coordinate $\Psi$, $\Psi_{ini}=0°$, $\Psi_{fin}=+180°$ from horizontal, $\Delta\Psi=180°$, M=32, N=180, P=N=180.

Antenna of the radiometric system mechanically revolves around rotational axis, the position of which in respect to the normal to the aperture plane by $\Phi$ coordinate has zero deviation, but by $\Theta$ coordinate may take up any values in the sector of angles from 0° to 90°, for example, coinciding with the first beam of the direction pattern by $\Theta$ coordinate. Then rotation axis and main direction of observation, which define the center of the image, have the following coordinates; $(\Theta_{main}=\Theta_{ini}=2°)$, $(\Theta_{main}=0)$.

Directions of reception $\theta_m$ correspond to orientation of axes for each of m beams of the directional pattern of antenna and are generated simultaneously in an antenna with dispersive properties of the radiometric system on the account of frequency division receiving directions by the spatial coordinate $\Theta$ info M independent directions through division of the general bandwidth of the radiometric system $\Delta f$, which, for example, has the width $\Delta f=14$ GHz into M narrower frequency bands $\Delta f_m$, which, for example, have the length $\Delta f_m=800$ MHz, each of which characterizes a separate receiving channel number m with the overall number of these channels M. At that the bandwidths of adjacent channels are partially overlapping.

The procedure of measurement in each of M receiving channels is comprised of sequentially executed operations of filtering and amplification of signals in ultra-high frequency range in a general for all receiving channels bandwidth $\Delta f=(f_{ini}-f_{fin})$, where $f_{ini}$ and $f_{fin}$ are, respectively, initial and final values of frequency of the radiation received by the radiometric system in ultra-high frequency range, for example, $f_{ini}=86$ GHz and $f_{fin}=100$ GHz, signal extraction in frequency band $\Delta f_m=(F_{m,ini}-f_{m,fin})$, where $f_{m,ini}$ and $f_{m,fin}$, respectively, are the initial and final values of frequency of the received radiation in the channel with number m associated to the range of ultra-high frequencies, at that, the mentioned values $f_{m,ini}$ and $f_{m,fin}$ are changing successively from channel to channel and are so selected that together, by $\Delta f_m$ bands in M receiving channels the whole frequency range $\Delta f$ is covered without omissions, and by independent directions $\theta_m$, corresponding to the $\Delta f_m$ bands, the whole sector of angles $\Delta\Theta$ is covered consistently and without omissions. This is provided, because the width of any from the M beams in direction pattern of the antenna by coordinate $\Theta$ is approximately twice larger than the angular distance between adjacent directions, i.e. $\Delta\theta\approx2(\theta_m-\theta_{m+1})$, for example, $\Delta\theta=1°$ and neighboring beams are partially overlapping. At last, measurement procedure is completed by consecutively executed in each channel operations of square-law detection, integration with $\tau_m$ integration interval, analog-digital conversion and digital accumulation.

Temporal phase of reception of external radiation with $\Delta t_{ex}$ duration, for example, $\Delta t_{ex}=1$ ms, is repeated P times in a sequence, for example, P=N, $\Delta t_{ac}=180$ ms, and during each element of this cycle 32-beam directional pattern of the antenna is oriented in a different from preceding direction $\psi_n$ by coordinate $\Psi$, for example, from $\Psi_{ini}=0°$ to $\Psi_{fin}=180°$ which defines propagation speed of the diagram ~1°/ms, and corresponds to velocity of circular rotation of the antenna ~2.8 revolutions/s and rotation period $T_{rev}=360$ ms.

Received on each interval $\Delta t_{ex}$ by M beams of the antenna M values of radio-thermal radiation intensity $E_{i,m}$, are processed in M receiving channels of the radiometric system concurrently and in accordance with the unified measurement procedure and transformed info a one-dimensional array of digital values $[C_m]$, which is entered into the memory of radiometric system's computer. At that the integration intervals in measurement channels $\tau_m$ are selected in accordance with proximity of spatial coordinates $\theta_m$ to the main direction of observation. Since in this example we selected an orientation of the rotational axis of the antenna coinciding with spatial orientation of the first beam $(\Theta_{main}=\Theta_{ini})$, then for the last 32-nd beam the accumulation interval will remain $\tau_{32}=\Delta t_{ex}=1$ ms, for 16-th beam, because of two times reduction of radius (perimeter of a circle), it is selected twice longer, $\tau_{16}=2\cdot\Delta t_{ex}=2$ ms, for 8-th beam, because of another twice reduction of the radius, it is selected 4 times longer, $\tau_8=4\cdot\Delta t_{ex}=4$ ms, for the fourth, respectively, 8 times longer, for second—16 times longer, and for the first beam—32 times longer $\tau_1=32\cdot\Delta t_{ex}=32$ ms. For intermediate numbers of beams that have not been mentioned here corresponding intermediate values of integration intervals are set, at that, the values of $\tau_m$ may, for example, be selected based on the following proportion:

$$\tau_m \leq \frac{\Delta t_{ex}\cdot|\Delta\Theta|}{N\cdot(|\Theta_{main}-\theta_m|+|\Delta\Theta|/M)}.$$

Length of the accumulation cycle $\Delta t_{ac}$ corresponds to rotation of the antenna by one-half turn, or by 180°, and obtained 180 one-dimensional arrays of values $[C_m]$ are transformed info a two-dimensional array of values $[C_{m,n}]$ with the number of dimensions [M, N]=[32, 180], which is entered into the memory of the computer of radiometric system.

Accumulation cycle $\Delta t_{ac}$, which is comprised of consecutively executed external radiation reception phases $\Delta t_{ex}$, is preceded by calibration phases by first and second calibration standards with duration $\Delta t_{cs1}$ and $\Delta t_{cs2}$, which are executed in any sequence, for example, $\Delta t_{cs2}=60$ ms. $\Delta t_{cs2}=60$ ms and initially is executed the calibration phase by first standard, then by the second. During the calibration phase by first standard direction pattern of the antenna is also moving by circular path, but the input waveguide of the radiometric receiver is disconnected from the antenna and connected to the output waveguide of the first calibrated standard. This operation may be executed, for example, with the use of controlled UHF switches. At that, M reception channels are simultaneously receiving the first calibration radiation with radiation intensities known for each channel $T_{c1,m}$ in units of the temperature scale, and the received signals are processed in M receiving channels concurrently and in accordance with unified measurement procedure, and are transformed into a one-dimensional array of digital values $[C_{c1,m}]$ with number of dimensions [M], which is entered into the memory of the computer of radiometric system. At that, integration intervals in measurement channels $\tau_m$ are selected in accordance with the duration of calibration phase $\tau_m \leq \Delta t_{cs1}$.

Upon completion of the calibration phase by first calibrating standard, calibration phase by second calibration standard $\Delta t_{cs2}$, is commenced, during which the direction pattern of the antenna also moves by circular path, however, input waveguide of radiometric receiver is disconnected from the first and connected to the output waveguide of the second calibration standard. This operation too is executed with the use of controlled UHF switches. Simultaneously M receiving channels are collecting the second calibration radiation with known intensity $T_{c2,m}$ in temperature scale units, and received signals are processed concurrently and in accordance with unified measurement procedure in M receiving channels and transformed into a one-dimensional array of digital values [$C_{c2,m}$] with number of dimensions [M], which is entered into the memory of the computer of radiometric system. At that, accumulation intervals in measurement channels $\tau_m$ are selected in accordance with the duration of calibration phase $\tau_m \leq \Delta t_{cs2}$.

Processing phase $\Delta t_{pr}$ is commenced upon the completion of accumulation cycle $\Delta t_{ac}$, for example, $\Delta t_{pr}$=40 ms. During this phase the direction pattern of the antenna continues its movement by the circular path, input waveguide of radiometric receiver is disconnected from the second calibration standard and reconnected to the antenna, however the signals on the outputs of receiving channels aren't used. During the processing phase $\Delta t_{pr}$ arrays of digital data [$C_{m,n}$], [$C_{c1,m}$], [$C_{c2,m}$], [$T_{c1,m}$], [$T_{c2,m}$], which were entered into the memory of the computer, are concurrent processed in accordance with data processing procedure in order to obtain brightness temperatures of the received radiation, as a result of which is generated a two-dimension array of values with number of dimensions [M, N], the values [$T_{b,m,n}$] of which, represented in temperature scale units, characterize two-dimensional distribution of the intensity of radio-thermal radiation $E_{i,m,n}$ which was received in the sector of spatial observation angles $\Delta\Theta \times \Delta\Psi$. Procedure of data processing too is comprised of consecutively executed operations of calculating for each of the m channels the $S_m=(T_{c1,m}-T_{c2,m})/(C_{c1,m}-C_{c2,m})$ values, which define the slope of linear dependence of transformation of output digital values $C_{m,n}$ into the values of brightness temperatures of outer radiation $T_{b,m,n}$, calculation of values $T_{b,m,n}$ according to found linear dependences in proportional denomination as $T_{b,m,n}=S_m \cdot (C_{m,n}-C_{c2,m})+T_{c2,m}$.

Upon completion of the processing phase $\Delta t_{pr}$, during the coordinate transformation phase $\Delta t_{tr}$ with duration of, for example, $\Delta t_{tr}$=20 ms, for two-dimensional array of brightness temperature values [$T_{b,m,n}$] it is executed the procedure of transformation of spatial coordinates of picture elements from the ($\Theta$, $\Psi$) coordinate grid into the ($\Theta$, $\Phi$) coordinate grid, if needed, coordinate transformation phase may be supplemented by the procedure, of transformation of the coordinates of picture elements from ($\Theta$, $\Phi$) coordinate grid into a linear coordinate grid (X,Y). Mentioned transformations of coordinates may be executed on the basis of known trigonometric formulae (see, for example, Spravochnik po matematike dlya ingenerov i uchaschikhsya VTUZov. Bronshteyn I. N., Somendyayev K. A., M.:Nauka, 1981, 704 p.)

Thus, complete execution cycle of the algorithm in this example of implementation starts with calibration phase by first standard $\Delta t_{cs1}$=60 ms, followed by calibration phase by second standard $\Delta t_{cs2}$=60 ms, then follows accumulation cycle $\Delta t_{ac}$=180 ms consisting of 180 consecutively executed phases of reception of external radiation $\Delta t_{ex}$ with duration of this phase equal to $\Delta t_{ex}$=1 ms, followed by the processing phase $\Delta t_{pr}$=40 ms, then coordinate transformation phase $\Delta t_{tr}$=20 ms. Total duration of one cycle of execution of the measurement algorithm, accumulation, processing and data transformation is 360 ms and is equal to the duration of one revolution $T_{rev}$ the antenna around its rotational axis. With that, direction pattern of the antenna makes a full revolution and returns to its initial position with the value of coordinate $\Psi_{ini}$=0°, and radiometric system generates an image which may be used for operative remotely sensed observations.

The mentioned algorithm may be repeated multiple times with continuous revolution of the antenna around its axes, as a result of which will be obtained a series of consecutive radiometric images. During temporal measurement of spatial orientation of the main direction of observation 4 on the account of auxiliary rotation of the whole antenna with the help of mechanical positioning devices, the images will be reflecting the changing observation conditions, at that, any part of the surrounding space may be consecutively observed.

In the considered example of implementation of the method for generation of radiometric images the algorithm is executed during one full revolution of the antenna around its rotational axis. At that, in the mentioned example the radiometric image is generated for half of the possible sector of observation angles by coordinate $\Psi$.

Other implementations are possible without affecting generality of claimed method, depending on selected duration of execution of calibration phases by first calibration standard $\Delta t_{cs1}$, calibration by second calibration standard $\Delta t_{cs2}$, reception of external radiation $\Delta t_{ex}$ in reference to period of revolution $T_{rev}$.

One alternate implementation of the method may be a combined operating sequence (see FIG. 6b), when during one revolution are executed the calibration phase by first and second calibration standards $\Delta t_{cs1}$, $\Delta t_{cs2}$, for example, $\Delta t_{cs1}=\Delta t_{cs2}$=90 ms and accumulation cycle $\Delta t_{ac}$ with duration, for example, $\Delta t_{ac}$=180 ms, and processing phase $\Delta t_{pr}$=40 ms and coordinate transformation $\Delta t_{pr}$=20 ms are executed concurrently and independently during the next period of revolution $T_{rev}$. In this case durations of calibration phases increase, which improves evaluation accuracy of calibration levels.

Another alternate implementation of the method may be a combined operating sequence (see FIG. 6c), when the group of consecutively executed calibration phase by first calibration standard $\Delta t_{cs1}$, calibration phase by second, calibration standard $\Delta t_{cs2}$, external radiation reception phases $\Delta t_{ex}$ (P=1) and processing phase $\Delta t_{pr}$ are cyclically executed I times consecutively, for example, I=N, N=360 with total duration of the mentioned cycle of N repetitions would be equal to revolution period $T_{rev}$, or 360 ms for the considered example. At that, aggregate duration of execution of the calibration phases by first calibration standard $\Delta t_{cs1}$, second calibration standard $\Delta t_{cs2}$ and external radiation reception phase $\Delta t_{ex}$ is equal for any element of the cycle with number i (I≥i≥1) and equal to 1/N part of the revolution period $T_{rev}$, for example, $\Delta t_{cs1}=\Delta t_{cs2}$=0.25 ms, $\Delta t_{ex}$=0.5 ms, and totally ~1 ms. Processing phase $\Delta t_{pr}$ with taking into account of I times reduction of the amount of computations for each element of the cycle may comprise, for example, $\Delta t_{pr}$=0.5 ms and executed concurrently during each consecutive i+1 element of the cycle. After this concurrently and independently, with each successive revolution of the antenna, is executed the coordinate transformation phase with duration $\Delta t_{tr}$, for example, $\Delta t_{tr}$=20 ms. In this alternate implementation of the method the image is generated for the whole sector of observation angles by coordinate $\Psi$=360° (circular image). The mentioned version is possible in the case of low internal noise of the radiometric system, which would allow the implementation of required radiometric sensitivity with short duration of calibration phases $\Delta t_{cs1}$ and $\Delta t_{cs2}$ and external radiation reception $\Delta t_{ex}$. A modification of this version would be such ratio of phase durations (see FIG. 6d), when during execution of each consecutive element of the cycle with number i (I≥i≥1) one of the mentioned two calibration phases by calibration standard $\Delta t_{cs1}$, or $\Delta t_{cs2}$ is sequentially excluded. Then the duration of each calibration phase and corresponding integration intervals $\tau_{cs1}$ and $\tau_{cs1}$ may be additionally increased two times by taking into account small volatility of calibration levels in close measurement time intervals. At that, if excluding the calibration phase by first calibration standard $\Delta t_{cs1}$ in cycle element with number (i) while execution of the processing phase $\Delta t_{pr}$, instead of array of values $[C_{c1,m}]$, $[T_{c1,m}]$ are used the mentioned arrays attained for (i−1) element of the cycle, and in the case of excluding the cycle element with number (i) calibration phase by second calibration standard $\Delta t_{cs2}$, during execution of the processing phase $\Delta t_{pr}$ instead of array values $[C_{c2,m}]$, $[T_{c2,m}]$ are used the mentioned arrays attained for (i−1) element of the cycle.

Taking into account small volatility of calibration levels in close measurement time intervals, instead of mentioned arrays for the current element of the cycle with number i (I≥i≥1) may also be used arithmetic mean values for each element of the above mentioned arrays, obtained by using K (K≥1), for example, K=8, significant previous values of these elements in K previous elements of the cycle, starting from number i. In this case, on the account of additional averaging of data $[C_{c1,m}]$, $[C_{c2,m}]$, accuracy of determining radiation levels from calibration standards is improved.

Figure 5:
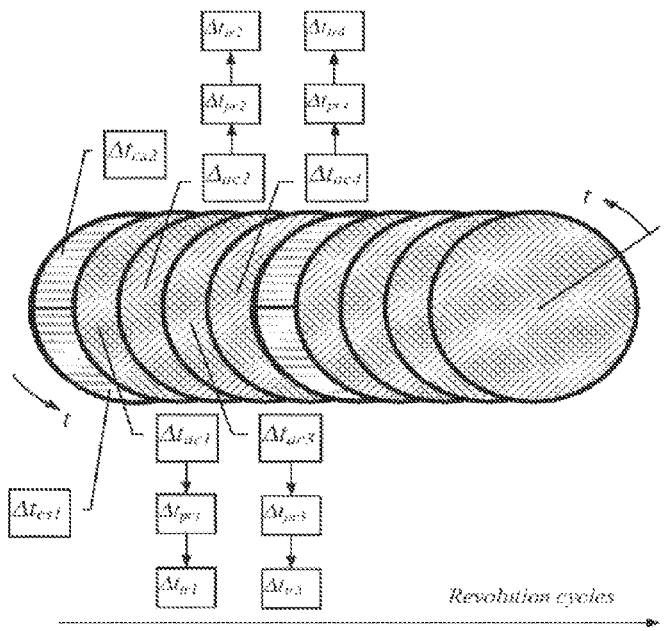
FIG. 5 illustrates the distribution of time intervals during execution of all procedures within a series of scanning cycles.
Figure 6:
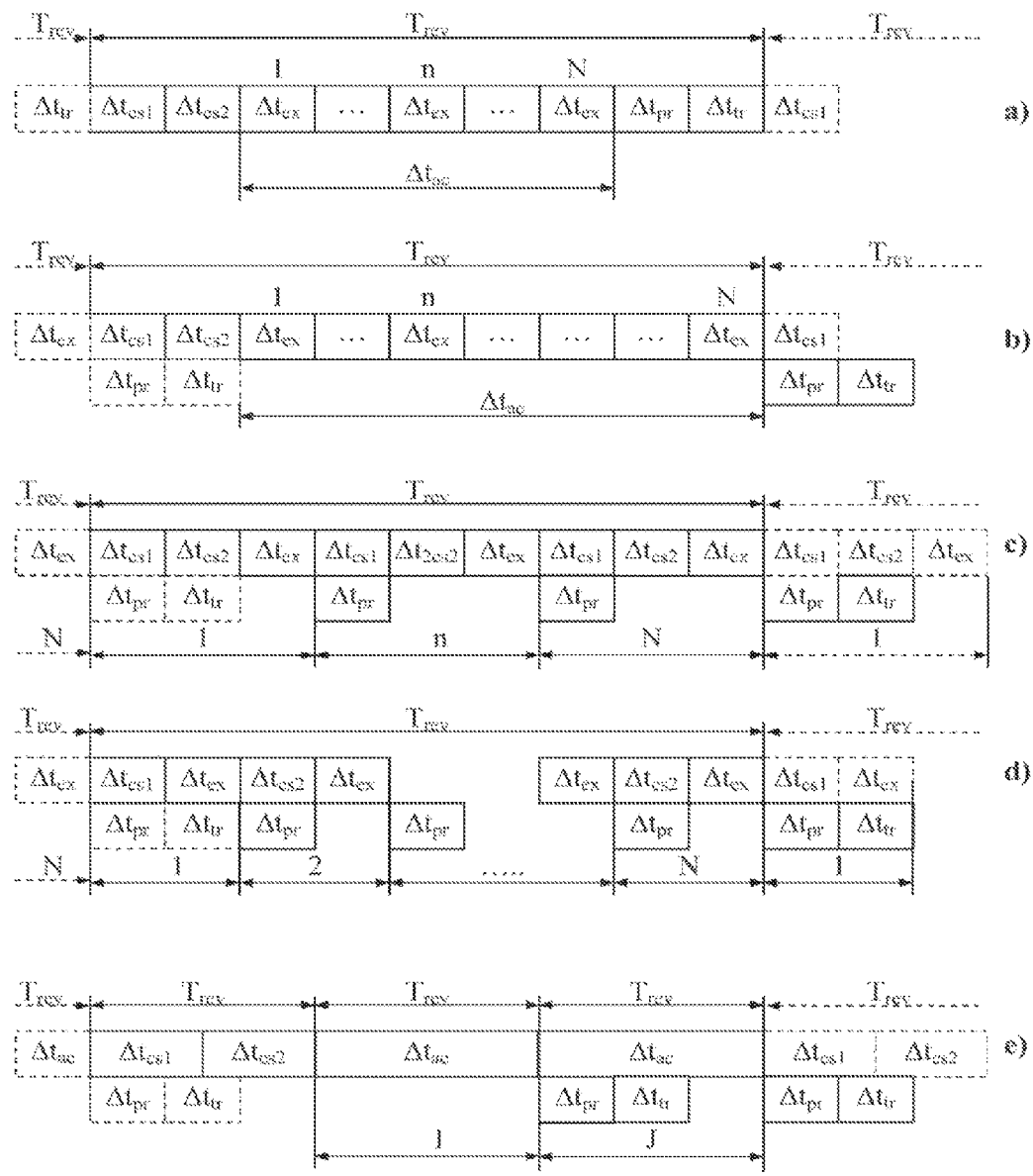
FIG. 6 illustrates the temporal cycle pattern of the algorithm during various proportions of durations of component procedures and rotational period of the antenna.

Yet another alternative implementation of the method may be a combined operating sequence (see FIG. 5, FIG. 6e), when calibration phase by first and second calibration standards $\Delta t_{cs1}$, $\Delta t_{cs2}$ are aggregately executed during one full revolution of the antenna $T_{rev}$, $\Delta t_{cs1}=\Delta t_{cs2}=180$ ms, and consecutively executed accumulation cycle $\Delta t_{ac}$, for example, from 360 consecutively repeated external radiation reception phases (N=360, $\Delta t_{ex}=1$ ms), processing phase $\Delta t_{pr}$ and coordinate transformation phase $\Delta t_{tr}$ form a group which is cyclically executed J times consecutively (J≥1), for example, J=4, at that, aggregate duration of the processing phase $\Delta t_{pr}$ and coordinate transformation phase $\Delta t_{tr}$ is shorter than revolution period $T_{rev}$ and they are executed independently from calibration phases $\Delta t_{cs1}$, $\Delta t_{cs2}$ and accumulation cycle $\Delta t_{ac}$ during the regular rotational period $T_{rev}$. At that, for all J generated images are used the same arrays of calibration values $C_{c1,m}$, $C_{c2,m}$. Thus, calibration phases $\Delta t_{cs1}$, $\Delta t_{cs2}$ are executed during the first revolution, then four (J=4) consecutive accumulation cycles $\Delta t_{ac}$ are executed, by one for each full revolution, and for each of these four cycles, during a fraction of next scanning period (revolution of the antenna) independently, four times, are executed the processing phase and data transformation phase $\Delta t_{pr}$ and $\Delta t_{tr}$, and as a result four images are generated in succession, after which the algorithm of implementation of the method is repeated.

On the assumption of anomalous multiplication of the internal noises of radiometric system on frequencies below 0.5÷1 Hz, calibration of radiometric system should be executed no not more often than once in a second (Hersman M. S., Poe G. A. Sensitivity of total power radiometer with periodical absolute calibration//IEEE Trans. on Microwave Theory and Tech. Vol. 29, No. 1, pp. 32-40, 1981), which, considering the rather high rotational speed of the antenna, for example, 5 rev/s (or 10 rev/s) will result in insignificant short intermissions in the process of image generation, with respective durations of 200 ms, (or 100 mc). At that, each fifth (tenth) image in the continuous series of generated images will be missing, and during a corresponding time interval the preceding fourth (ninth) image may be reproduced one more time, which will not affect significantly on the efficiency of image generation process and data analysis.

In considered examples of implementation of the method the main direction of observation $\Theta_{main}$ coincides with one of the outer beams of the antenna in the sector $\Delta\Theta$. Without transgression of generality we may also consider alternate implementations when the main direction of observation $\Theta_{main}$ by coordinate $\Theta$ takes up any values in the sector of angles from 0° to 90°. In the case, when main direction of observation $\Theta_{main}$ is inside the sector $\Delta\Theta$, there appear two groups of beams revolving with equal velocities, which are situated along common moving line but are generating images of different diameters. During transposition of these images and element averaging radiometric resolution in the central part of the image may be additionally improved on the account of constriction of the sector of observation angles. If $\Theta_{main}$ is positioned in the middle of the sector $\Delta\Theta$, the diameters of these images will coincide. Then, on the account of 2 times constriction of the sector of observation angles either the frequency of image generation may be doubled, for the selected period of revolution $T_{rev}$, or, with the same frequency of image, generation, on the account of their paired averaging, the equivalent integration interval may be doubled $\tau_{me}=2\tau_m$.

If the main direction of observation $\Theta_{main}$ by coordinate $\Theta$ takes up a value situated outside the sector of angles $\Delta\Theta$, than inside the generated images appears an empty area, which may be filled up during linear motion of the antenna with a coordinated velocity, in this, case an alternate version of image generation with multiple-beam conical scanning may be implemented, for example, while mapping the surface from the board of a flight vehicle (see FIG. 7).

As a device which would implement all the procedures of measuring, accumulating and processing the data, executed in the above mentioned sequence during the mentioned phases of execution $\Delta t_{cs1}$, $\Delta t_{cs2}$, $\Delta t_{ac}$, $\Delta t_{pr}$ and $\Delta t_{tr}$, may be used the known multiple-beam scanning radiometer (Patent UA 56347) which possesses a full-featured set of required functions, set of required elements and a corresponding structure of internal communications. At that, the antenna from the second invention from the group in present claim is used as the antenna for this radiometer.

The antenna contains (see FIG. 1) pedestal unit 1, electromechanical transmission 2, the stator section of which 2-1 is rigidly connected to the pedestal unit 1 by bracing elements 3, and rotor section with the output shaft 2-2 is isochronously revolving around its axis, for example, counterclockwise, defining the main rotational axis 4, a rotating waveguide transition 5, comprised of stationary stator section 5-1 which is rigidly connected to the pedestal unit 1 and moving rotor section 5-2 which is rigidly connected to the output shaft of the electromechanical transmission 2-2, canceller of angular momentum 6, connected, through kinematic transmission, with the output shaft 2-2 electromechanical transmission 2 and rotating in the opposite direction to the shaft, a planar dielectric waveguide 7 and two-dimensional diffraction grating 8, irradiator 9, and position sensor 10, mounted on the pedestal unit 1, at that, input of the irradiator 9 is connected to the output of planar dielectric waveguide 7, output of the irradiator 9 is connected to the waveguide input of the movable rotor section 5-2 of the revolving waveguide transition 5, controllable input of electromechanical transmission 2 and output of the position sensor 10 are, respectively, controllable input and output of the antenna, and waveguide, output of the stator section 5-1 of the revolving waveguide transition 5 is the output of the antenna, at that, planar dielectric waveguide 7 and two-dimensional diffraction grating 8 are electrodynamically connected with each other by the diffraction field in the range of working frequencies of the antenna $\Delta f=(f_{ini}-f_{fin})$, where $f_{ini}$ and $f_{fin}$ respectively, are the initial and final values of the frequency of electromagnetic radiation received by the antenna, at that, while band splitting $\Delta f$ into M (M≥1) narrower bands $\Delta f_m$ (1≤m≤M) in coordinate grid $\Theta$ form in the space M-beam fan-shaped direction pattern with M beams 11-m the axes of which in coordinate plane $\Theta$ are forming the observation directions $\theta_m$, side of the planar dielectric waveguide 7, on which falls the received radiation, is the receiver aperture plane, planar dielectric waveguide 7, two-dimensional diffraction grating 8 and irradiator 9 are mechanically rigidly connected to each other and form a unified constructional assembly, which is named rotor of the antenna, and the mentioned rotor of the antenna is mechanically rigidly connected to the output shaft 2-2 of the electromechanical transmission 2 (not shown on FIG. 1), at that position sensor 10 is connected to the rotor of the antenna, the informational parameter of the output signal of the position sensor 10 is connected with angular position of the rotor of the antenna while it is revolving around its main axis 4.

In order to create a multiple-beam direction pattern 11 in the mentioned antenna, it, as a constituent part of the scanning antenna, is used as a part of known multiple-beam UHF-radiometer (exemplified in Patent (UA) No 56347), providing band splitting of $\Delta f$ frequencies into M frequency bands $\Delta f_m$ for the radio-thermal radiation received by the scanning antenna, at that by its output, controllable inputs and the output the scanning antenna should be connected to the input, controllable output and input of corresponding elements of the mentioned multiple-beam scanning UHF-radiometer. All comprising elements of the mentioned multiple-beam scanning UHF-radiometer with mentioned internal connections, except for scanning antenna, are shown on FIG. 1 as multiple-channel radiometric receiver 12, which generates images, which may be represented in circular 13 and square 14 coordinate grids.

As the pedestal unit 1 may be used any stationary base which has an alignment plane for the attachment of comprising elements of scanning antenna and providing an unfaltering space orientation of the main rotational axis 4 and electromechanical transmission 2 during the process of operation. As the pedestal unit 1 can also be used any supporting and turning arrangement possessing an alignment plane for the attachment of comprising elements of scanning antenna and providing, in the process of operation, operator-controlled manual or automatic, executed based on the operator's commands, correction of spatial orientation of its alignment pane. For example, in place of such pedestal unit can be used a tripod used by television operators for installation and control of the position of professional video cameras, for example, a tripod with manual control.

As the electromechanical transmission 2 may be used any mechanical transmission with hollow shaft 2-2, which can provide direct, or reduced synchronized isochronous revolution of the shaft and connected to the shaft elements with a given speed. At that, the input of the control line of the transmission is controllable input of the electromechanical transmission 2. For example, Patent (UA) No 56347 discloses an electromechanical transmission that may be realized en the basis of reduced stepper-motor. In this case it consists of a mechanically linked stepper motor and reducing gear, as well as pulsed amplifiers for the stepper motor control signals, with their number corresponding to the number of phase coils of the stepper motor, at that, each of the pulsed amplifiers is series-connected between the corresponding line of the input bus of the transmission 2 and the appropriate connector of the phase coil of the stepper motor. At that, inputs of the driver amplifiers and output shaft of the reducing gear are, respectively, the input of the control bus and shaft of the electromechanical transmission 2.

As bracing elements 3 may be used any known elements, for example, thread connection elements.

As revolving waveguide transition 5 may be used any known type of rotating waveguide linkage joint that will provide transmission of electromagnetic energy from its rotating waveguide input into its stationary waveguide output with small losses in the working bandwidth $\Delta f$ of scanning antenna. For example, in place of rotating waveguide transition may be used the rotating waveguide linkage joint described in (Buduris J., Chenevie P. Ultra-high frequency chains (Theory and application). Translation from French./Editor A. L. Zinovieva.—M.:Sov. Radio, 1979,-288 p., pp. 130) and comprising an input and output sections of hollow rectangular waveguides, each of which has on its wide wall transition elements to a circular waveguide with transformation of the main wave $H_{01}$ in the rectangular waveguide into the $E_{01}$ wave of the circular waveguide. At that, the mentioned sections of circular waveguides are situated axially with the rotation axis and form a waveguide line with a rotary joint and a circular gap on the wall of the circular waveguide; electrical interlocking for ultra-high frequency currents is provided with the help of quarter-wave traps in the area of rotary joint. When using this type of waveguide joint in place of rotating waveguide transition 5, its transmission link based on circular waveguide with rotary joint installed inside of the hollow output shaft 2-2 of the electromechanical transmission 2, axially with the main rotational axis 4, one of the sections of rectangular waveguide are rigidly connected to the shaft 2-2, its waveguide flange is the waveguide input of the moving rotor section 5-2 of the transition 5, and second section of the rectangular waveguide is rigidly fixed on the basis 1, its waveguide flange is the waveguide output of the stator section 5-1 of the transition 5.

Canceller of angular momentum 6 is designated for compensation of angular momentum of the antenna rotor in the process of high-speed revolution, which makes difficult to change the spatial position of the main axis 4 because of gyroscopic action. An example of the structure of a canceller of angular momentum 8 is shown in FIG. 8. In place of angular momentum canceller 6 may be used any engineering solution that will provide for isochronous revolution of some body with the mass $M_{con}$ with given angular speed $\omega_{con}$ and under certain efficient rotation radius $R_{con}$ in the direction opposite to the canceled angular momentum of the antenna rotor. For example, such canceller may be created by kinematic scheme shown on FIG. 6, and will comprise a transmission gear 15 positioned on the output shaft 2-2, electromechanical transmission 2, intermediary gear 16, the axis 17 of which is rigidly fixed on base 1, and disk 18 with the central bearing to provide free rotation of the disk 18 around shaft 2-2, at that, disk 18 has driving surface 19 corresponding to the working surface of gear 16. This device would provide for revolution of the disk with mass $M_{con}$ and effective, radius $R_{con}$ in the direction opposite to revolution of the shaft 2-2 with angular velocity, which is defined by angular rotation speed of the shaft 2-2 and transmission coefficient $K_{con}$ of the mentioned kinematic scheme. On the account of selecting the mass of the disk $M_{con}$, its radius $R_{con}$ and transmission coefficient $K_{con}$ of the kinematic scheme it is possible to provide complete cancellation of angular momentum of the antenna rotor when it is rotating with constant velocity around the axis 4, which would allow to change the spatial orientation of the main axis 4 in the process of scanning of the antenna.

Planar dielectric waveguide 7 and diffraction grating 8 may be accomplished in accordance with known engineering solutions (see, for example, Skaniruyuschaya antenna samoletnogo radiometricheskogo kompleksa/Andrenko S. D., Evdokimov A. P., Kryzhanovskiy V. V., Provalov S. A., Sidorenko Yu. B.//Radiofizicheskiye metody I sredstva dlya issledovanlyaokruzhayuschey sredy v millimetrovom diapazone.: Sb.nauch, tr.—Kiev: Nauk, dumka, 1988.—s. 154-160). For example, planar dielectric waveguide 7 may be fabricated from a polystyrene sheet of given thickness with the use of mechanical plane grinding technology. Diffraction grating 8 may be accomplished as a flat metallic comb with lateral dimensions defined in an orthogonal coordinate base X and Y; the grating has a periodic structure by X coordinate and a flat structure by the Y coordinate. At that, coordinate plane Θ of the directional pattern of antenna coincides with the coordinate axis X and is orthogonal to coordinate axis Y. Dielectric waveguide 7 is located on some distance Δ from the periodic structure of the diffraction grating 8 and is linked to it by diffraction field. In order to create the given amplitude-phase distribution of the field by X coordinate the distance between the grating and the waveguide is selected during the alignment process and may change slightly by X coordinate.

Irradiator 9 may be accomplished in accordance with any known engineering solution for the exciter of planar dielectric waveguide providing a given transverse field structure at the interface with dielectric waveguide of selected aperture and concentration of electromagnetic energy on the output flange of the irradiator 9 with the structure of field for the main wave $H_{01}$ of the standard hollow metallic waveguide. In place of irradiator 9 may be used a horn feeder or horn-parabolic exciter (see, for example, Skaniruyuschaya antenna samoletnogo radiometricheskogo kompleksa/Andrenko S. D., Evdokimov A. P., Kryzhanovskiy V. V., Provalov S. A., Sidorenko Yu. B.//Radiofizicheskiye melody I sredstva dlya issledovaniyaokruzhayuschey sredy v millimetrovom diapazone.: Sb.nauch, tr.—Kiev: Nauk, dumka, 1988.—s. 154-160), providing a single transmitting mode of electromagnetic energy. An additional design requirement to irradiator 9 in this antenna is the need of consecutive turning of the wave propagation direction by 90°, two times, which simplifies the placement of output flange of the irradiator 9 on the back side of the diffraction grating 8 near rotational axis 4, providing the size of the antenna rotor in the rotation plane to be maximally close to the aperture of diffraction grating 8, thus reducing the size of the antenna rotor.

Position sensor 10 may be accomplished on the basis of any engineering solutions providing generation of pulsed electric signal while given spatial position of the controlled object is attained, for example, based on a magnetic sensor. At that, on one of the construction elements of the antenna rotor, for example, on the back side of the diffraction grating 8 is placed a permanent magnet, and on the pedestal unit 1 near the circular path of rotation of the magnet is positioned an inductive coil, which is part of the oscillating circuit of an electronic generator. During the passage of the magnet the frequency of the generator changes, thus operating the comparator, which generates the output signal of the position sensor 10.

Parameter values during consideration of the antenna system were used the abovementioned values of these parameters on the example of implementation of the method for generation of radiometric images by first invention.

Figure 1:
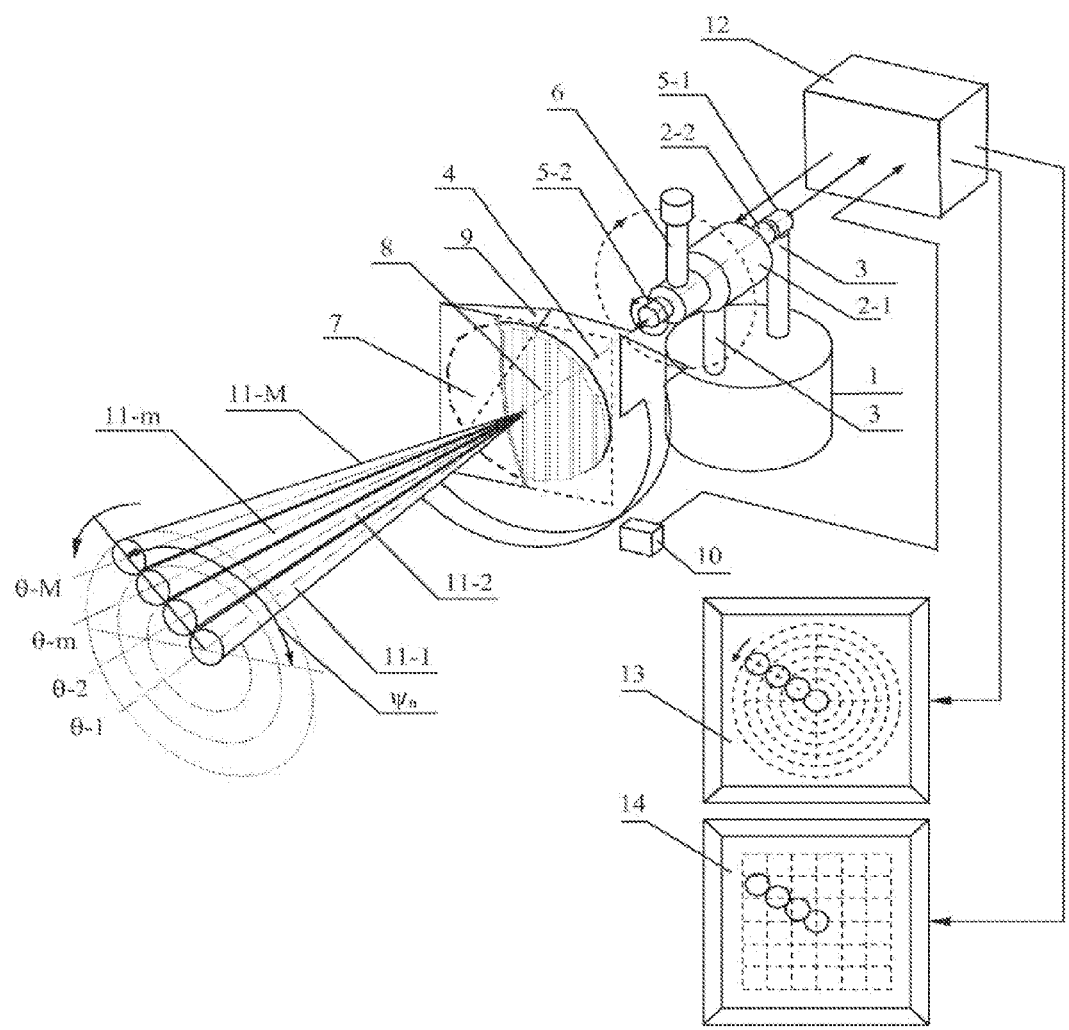
Figure 2:
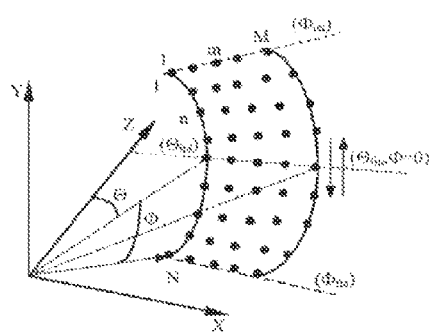
Figure 3:
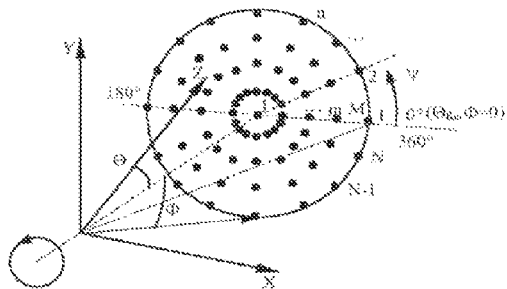
Figure 4:
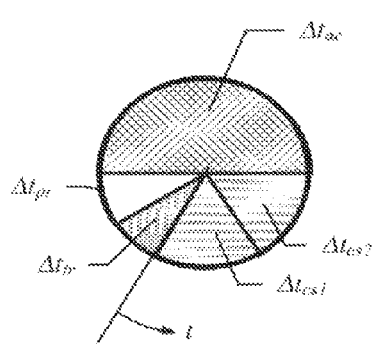
FIG. 4 illustrates the distribution of time intervals during execution of all procedures within a single scanning cycle.

The antenna operates in the following way (see FIG. 1). Under the influence of the control signal applied to the controlling input of the antenna from multiple channel radiometric receiver 12, the shaft 2-2 of the electromechanical transmission 2 is rotating with constant angular velocity, for example, ~2.8 rot/s with the rotation period $T_{rev}$=360 ms, as a result of which the antenna rotor, which is connected to shaft 2-2, is rotating wilt) the same angular velocity. External radio-thermal radiation is falling under various angles on the aperture plane of the antenna, which is defined by external surface of the planar dielectric waveguide 7, passing through the planar dielectric waveguide 7 and scattering on diffraction grating 8, Parameters of the open electrodynamic structure formed by the dielectric waveguide 7 and diffraction grating 8 are selected in such a way, that in the Δf band the radio-thermal radiation, which is entering at every moment of time from certain spatial angle is transformed into a planar wave in dielectric waveguide 7, which is channeled through the irradiator 9 and rotating waveguide transition 5 to the input of radiometric receiver 12. At any moment of time the mentioned spatial angle is defined by spatial position of the sector of angles ΔΘ×ΔΦ which are calculated from the normal to the aperture plane of the antenna and spatially associated with the local coordinate grid, oriented in the aperture plane and defining its spatial position. At that, one axis ($\bar{z}$) of the coordinate grid is situated perpendicularly to the aperture plane of the antenna, the second axis ($\bar{x}$) lies in the aperture plane and defines the direction of propagation of the received electromagnetic wave in planar dielectric waveguide 7, and the third axis ($\bar{y}$) is orthogonal to the mentioned two axes and defines the orientation of scattering elements (combs) of the diffraction grating 8.

Receiver 12 provides band splitting of frequencies Δf of the received radio-thermal radiation into M frequency hands $\Delta f_m$. On the account of expressed dispersion properties of mentioned open electrodynamic system of the antenna, in each of M received frequency bands $\Delta f_m$ in the sector of angles ΔΘ×ΔΦ transformation of the falling radio-thermal radiation is accomplished with varying efficiency. As a result, at each given moment of time the antenna by angular coordinate Θ, calculated from $\bar{z}$ axis in the (X0Z) plane, an M-beam direction pattern 11 is formed with M most efficient directions of reception $\theta_m$, defining the spatial positions of axes for the M beams of the directional pattern of antenna. At that each of the directions $\theta_m$ is unequivocally associated with a corresponding band of frequencies $\Delta f_m$. Since the dispersion properties of electrodynamic system of the antenna are only expressed in one direction associated with the coordinate axis Θ, by second angular coordinate Φ, which is calculated from $\bar{z}$ axis in (Y0Z) plane, all 11-$m$ beams have equal width Δϕ which is defined by cross-section size of the diffraction grating 8 by corresponding spatial coordinate Y. Thus, ΔΦ=Δϕ, for example, Δϕ=1°.

As a result of rotation of the antenna rotor, the M-beam direction pattern also rotates synchronously, and each of 11-$m$ beams is moving by its cone-shaped moving line depending on deviation $\theta_m$ of the particular beam 11-$m$ from the selected main direction of observation $\Theta_{main}$ in the plain of values Θ. For example, initial orientation of the aperture plane of the antenna and main rotational axis 4 may be selected in such a way that one of the outer beams in M-beam direction pattern would coincide in direction with the axis 4. While turning the M-beam direction pattern in full rotation angle Ψ equal to 360°, the antenna has full view of cone-shaped sector of spatial angles, which has, in place of its spatial axis, the main rotational axis 4 and the aperture at the vertex of a cone is 2ΔΘ.

In the process of scanning angular momentum of the antenna rotor is fully cancelled on the account of turning in the opposite direction and with required speed the angular momentum canceller 6. At that, spatial orientation of the sector of observation angles of the antenna can be changed without any significant effort by means of changing the spatial orientation of the alignment plane of the pedestal unit 1.

Independent angular positions of the antenna rotor in time are rigidly linked with the structure of controlling signal entering the electromechanical transmission 2 from radiometric receiver 12. As a result, it is provided synchronization of data in receiver 12 and mutual spatial binding of responses of receiver 12 to the received radio-thermal radiation to current spatial positions of the M-beam direction pattern.

With each full revolution of the antenna rotor position sensor 10 generates a pulsed signal, which enters the radiometric receiver 12. On the account of this is provided the initial temporal synchronization of signals in radiometric receiver 12, and on its output it generates an array of output values of brightness temperatures, which represents the intensify distribution of radio-thermal radiation in spatial sector of observation angles in temperature scale units. At that, the image may be generated both in an angular coordinate system 13, associated with the rotational axis 4, and in an rectangular coordinate system 14, associated with external, in respect to the antenna, reference system.

FIGS. 9a to 9d show a number of different configurations of the dielectric waveguide 7 and the irradiator 9. Any of the configurations illustrated may be incorporated into any of the antenna configurations shown in FIG. 10. In FIG. 9a, the irradiator 9 takes the form of a plane metal hollow irradiator and the dielectric waveguide is substantially rectilinear when viewed from above. In FIG. 9b the dielectric waveguide 7 is elongate and tapered. The variant shown in FIG. 9c has a parabolic configuration. A metallic film is provided on the parabolic edge 20 of the dielectric waveguide 7 in order to provide reflection of the internal electromagnetic wave of the dielectric waveguide 7 into irradiator 9. FIG. 9d shows a parabolic hollow metallic irradiator configuration.

Figure 10A:
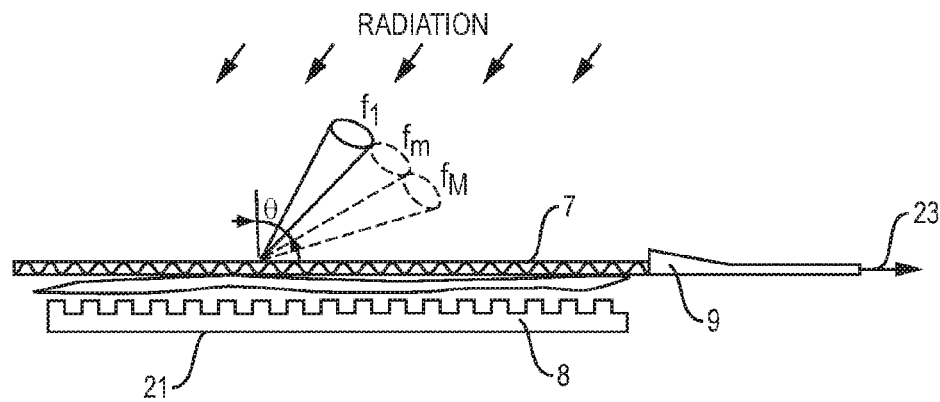

FIGS. 10a to 10e show a number of different configurations of the antenna 22 of which the dielectric waveguide 7 and the irradiator 9 form a part, in each case, as shown only in FIG. 10a for clarity, radiation is incident on the antenna from above. Radiation from a cone of rays at the frequencies $f_1$, $f_m$, $f_M$ at changing angles of $\theta_1$, $\theta_m$, $\theta_M$ measured from the normal to the plane of the dielectric waveguide 7 is incident on each point of the dielectric waveguide 7. Also illustrated on FIG. 10a is the surface wave 21 that results from the transformation of the electromagnetic waves incident on the diffraction grating 8.

FIG. 10a shows a configuration in which the diffraction grating 8 is parallel to the dielectric waveguide 7. The dielectric waveguide 7 is at least coterminous with the diffraction grating. The surface wave 21 is induced into the dielectric waveguide 7, passes through the irradiator 9 and out of the antenna 22 in the direction indicated by the arrow 23.

Figure 10B:
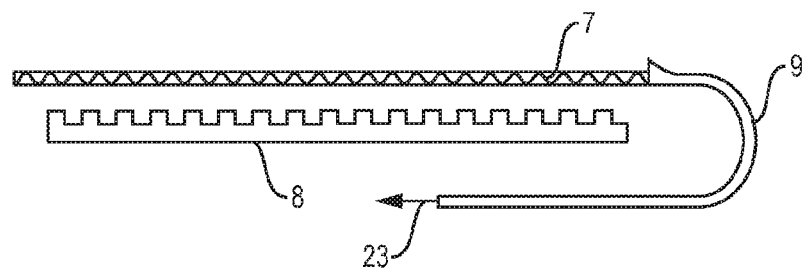
Figure 10C:
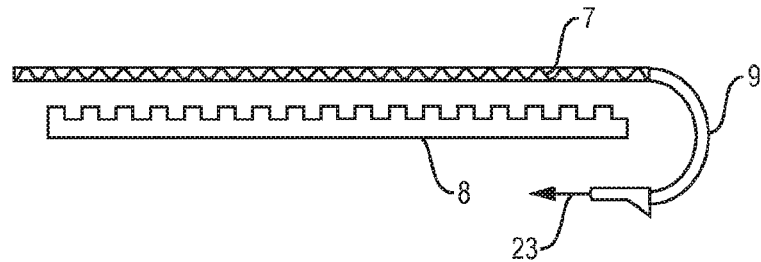

FIGS. 10b and 10c show two configurations in which the irradiator 9 and dielectric waveguide 7 cause the output signal from the antenna 23 to be output behind the diffraction grating 8. These two configurations reduce the required extent of the antenna 22 in the horizontal plane (as illustrated in FIG. 10). The configuration shown in FIG. 10b has a hollow metallic irradiator 9, for example the parabolic configuration shown in FIG. 9d. The configuration shown in FIG. 10c has an elongate dielectric waveguide which can be provided with a metallic film on the parabolic edge 20 in accordance with the configuration shown in FIG. 9c.

Figure 10D:
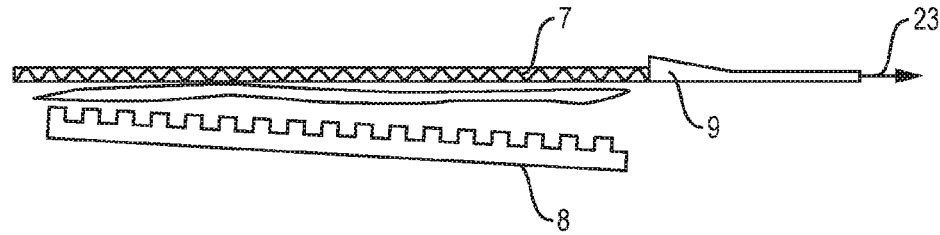

FIG. 10d shows a configuration in which the diffraction grating 8 is non-parallel with the dielectric waveguide 7. In the illustrated configuration, the diffraction grating 8 and the dielectric waveguide 7 are both planar; therefore the distance between them increases at a constant rate. However, in alternative examples, not illustrated, the gap between the dielectric waveguide and the diffraction grating may change in a smooth but non-linear manner. A non-parallel configuration provides a better electromagnetic field distribution across the diffraction grating that result in a reduction in side lobes for this configuration, in order to maximize this effect, the point of greatest separation between the dielectric waveguide 7 and the diffraction grating should be adjacent the irradiator 9.

Figure 10E:
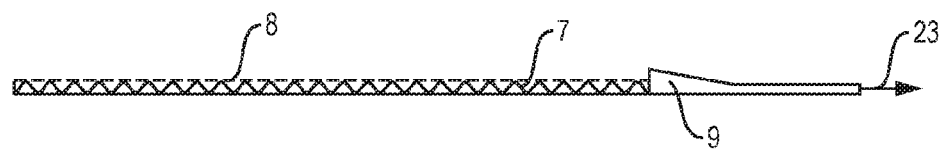

FIG. 10e shows a configuration in which the diffraction grating 8 and the dielectric waveguide 7 are provided on a common substrate. This configuration is advantageous for packaging of the antenna in applications when space is at a premium as the antenna formed in this way occupies a reduced volume and weight.

FIGS. 11a to 11f show different configurations of part of an imaging unit including an antenna as shown in any of FIGS. 10a to 10e. In all of the illustrated configurations the antenna 22 comprises ail of the components described above with reference to FIG. 1. However, for the sake of clarity, only the irradiator 9 and the rotating wave-guide transition 5 are shown in the various configurations illustrated in FIG. 11. Following the calibration, which may be carried out using different configurations as will be described below, the signal is passed through a band filter 40 and a low noise amplifier 42 before being mixed in a first mixer 44 in combination from an input from a first heterodyne 46. Following the mixing, the signal is then passed through an intermediate frequency amplifier 48.

In the example shown in FIG. 11a, the calibration standards 31, 32 are provided via a first switch 33 and a second switch 34. These are configured to allow the calibration standards to be introduced into the system directly at the output of the antenna, before the band filter.

In the example shown in FIG. 11b, the calibration is provided by a noise generator 35 and an attenuator 38 and is introduced into the system using a directional coupler 37 after the first switch 33, in this example, the noise generator 35 works in a binary on/off configuration.

In the example shown in FIG. 11c, the noise generator 35 is introduced via a directional coupler 37 directly to the output of the antenna, prior to the first switch 33 that in "off" position works as attenuator for calibrating signal of noise generator 85. In this example, the noise generator also 35 works in a binary "on/off" configuration.

In the example shown in FIG. 11d, the calibration occurs directly within the irradiator 9. The directional coupler 37 is provided on one side of the parabolic portion of the irradiator 9 or dielectric waveguide 7. The example shown in FIG. 11e is a further development of that shown in FIG. 11d as the calibration occurs directly within the irradiator 9 as a result of input directly into the irradiator 9. In addition, the band filter is provided directly on the output of the antenna 22 and a further low noise amplifier 38 is included prior to the first switch 33 that reduces the noise of the system.

The example shown in FIG. 11f incorporates all of the above described features into the antenna 22. As a result of this radical change in configuration, the output from the irradiator 9 is fed directly to the band filter 40, low noise amplifiers 38, 42, first switch 33, first heterodyne 46, first mixer 44 and intermediate frequency amplifier 48 before being introduced into the rotating wave-guide transition 5. In this case the transition is coaxial which results in cost reduction and simplification of the system. In addition, removal of the wave guide rotating transition from the input of low noise amplifier 38 reduces noise figure of the system due to this transition active loss elimination.

FIG. 12 shows one example of a device incorporating the imaging unit according to the present invention. The back view of the device is shown in FIG. 12a, the side view of the device is shown in FIG. 12b, the front view in FIG. 12c and a cross section through the device is shown in FIG. 12d. The device 100 is a handheld imaging unit provided with a lens 102 of diameter 300 mm. The device 100 has a housing that includes a head portion 101 sized to accommodate the lens 102. An elongate housing portion 114 extends substantially perpendicular to the head portion 101. A handle 103 extends from the elongate portion 114 to enable the device 100 to be held conveniently by a user, in addition to housing the lens 102, the head portion 101 also incorporates an antenna 22 as described above, a low noise amplifier 42, calibration unit 104 and the required high frequency and low frequency electronics 105. The rotation of the antenna 22 is controlled by the motor 106, moderated by motor electronics 108 and triggered by the user activating the trigger 110. A data processing unit 112, configured to execute the data processing phase, is contained within the elongate housing portion 114 which also houses the power electronics 116.

In addition to the functionality of the imaging unit as described above, the device 100 includes a video camera 118, illumination 120, a GSM antenna 122 and a flash memory and removable memory card 124. The illumination 120 takes the form of a plurality of LEDs spaced around the periphery of the lens 102. The data from the video camera 118 and the GSM antenna 122 is processed by suitable video and GSM link electronics 126. The image data arising from the processed antenna data, together with the data from the video camera 118 can be stored in the memory and/or on the card 124 or transferred using a GSM link to a remote location for storage or further processing. Control of the device 100, including control of the transfer of data and combined real time optic/radiometric images is executed using a touch screen 128 in combination with a headset and microphone 129. The touch screen 128 is configured so that it is visible to the user when holding the device 100. The headset and microphone 129 are connected info the device 100, either physically or via a Blue tooth or similar wireless protocol. The memory card 124 is conveniently located within the handle 103 which can be provided with an access port (not shown) to allow the memory card 124 to be changed.

The power for the device 100 may be incorporated into the device housing. However, batteries can add considerably to the weight of the device and therefore, for ease of use the batteries may be provided in a separate pack 130 which the user may wear around the waist. The battery pack 130 will be attached to the device at a power plug 132.

The invention is not limited for use at the hand-held scale. Indeed, with an increase in aperture size and an increase in range a similar device could be used for covert defection or to aid landing of helicopters.

The invention claimed is:

1. A method of radiometric image generation using a series of isochronous revolutions of a multi-beam, scanning antenna with a dispersion characteristic, wherein the antenna is combined with a multi-channel receiver with frequency channel separation to form an imaging unit, the method comprising cyclically executing the following phases:
 two separate calibration phases $\Delta t_{cs1}$, $\Delta t_{cs2}$ using first and second standards;
 external radiation reception phase $\Delta t_{ex}$,
 data processing phase $\Delta t_{pr}$, and
 data transformation phase $\Delta t_{tr}$.

2. The method according to claim 1, wherein the reception phase of the external radiation $\Delta t_{ex}$ is executed consecutively P (P≥1) times forming an accumulation cycle $\Delta t_{ac}$ with a duration $P \cdot \Delta t_{ex}$.

3. The method according to claim 2, wherein the total duration of the calibration phase by the first calibration standard $\Delta t_{cs1}$, the calibration phase by the second calibration standard $\Delta t_{cs2}$, the accumulation cycle $\Delta t_{ac}$, processing phase $\Delta t_{pr}$ and coordinate transformation phase $\Delta t_{tr}$, executed consecutively is equal to the rotation time period $T_{rev}$ of the antenna.

4. The method according to claim 2, wherein the total duration of the calibration phase by the first calibration standard $\Delta t_{cs1}$, the calibration phase by the second calibration standard $\Delta t_{cs2}$, the accumulation cycle $\Delta t_{ac}$ executed consecutively is equal to the rotation time period $T_{rev}$ of the antenna.

5. The method according to claim 2, wherein the total duration of the consecutively executed calibration phase by the first calibration standard $\Delta t_{cs1}$ and the calibration phase by the second calibration standard $\Delta t_{cs2}$, is equal to rotation time period $T_{rev}$ and wherein the consecutively executed accumulation cycle $\Delta t_{ac}$, processing phase $\Delta t_{pr}$ and coordinate transformation phase $\Delta t_{tr}$ is executed cyclically J times in a row (J≥1), and wherein the data processing phase $\Delta t_{pr}$ and coordinate transformation phase $\Delta t_{tr}$ have a total duration which is less than rotation time period $T_{rev}$ and are executed independently from the calibration phases $\Delta t_{cs1}$, $\Delta t_{cs2}$ and accumulation cycle $\Delta t_{ac}$ within the time limits of the next rotation time period $T_{rev}$.

6. The method according to claim 2, wherein the capacity of expansion measure for accumulation cycle $\tau_m$ within the time period of external radiation reception $\Delta t_{ex}$, in accordance with the proximity of spatial coordinates $\theta_m$ to the main direction of observation $\Theta_{main}$, the following expression is used $$\tau_m \leq \frac{\Delta t_{ex} \cdot |\Delta\Theta|}{N \cdot (|\Theta_{main} - \theta_m| + |\Delta\Theta|/M)}.$$

7. The method according to claim 1, wherein the consecutively executed calibration phase by the first calibration standard $\Delta t_{cs1}$, calibration phase by the second calibration standard $\Delta t_{cs2}$, reception phase of external radiation $\Delta t_{ex}$ (P=1) and processing phase $\Delta t_{pr}$ is performed cyclically N times in a row (I=N, where N is number of independent beam positions per revolution), with a total duration of the mentioned cycle of N repetitions equal to the rotation time period $T_{rev}$.

8. The method according to claim 7, wherein the coordinate transformation phase $\Delta t_{tr}$ is subsequently executed independently.

9. The method according to claim 7, wherein in the course of execution of each regular element of the cycle with a number i (I≥i≥1) each of the calibration phases is alternately excluded, and in the course of execution of processing phase $\Delta t_{pr}$ the data is obtained for the (i−1) element of the cycle.

10. The method according to claim 1, wherein the total duration of the execution of calibration phases by the first calibration standard $\Delta t_{cs1}$, by the second calibration standard $\Delta t_{cs2}$ and reception of external radiation $\Delta t_{ex}$ is the same for any element of the cycle with a number i (I≥i≥1) and is equal to the $(1/N)^{th}$ part of the rotation period $T_{rev}$, and the processing phase $\Delta t_{pr}$ is executed independently in the course of regular $(i+1)^{th}$ element of the cycle.

11. The method according to claim 1, wherein the values of $[C_{c1,m}]$, $[T_{c1,m}]$, and $[C_{c2,m}]$ $[T_{c2,m}]$ data array elements for the current element of the cycle under number i (I≥i≥1) are the mean arithmetic values for each element of these data arrays, obtained by utilization of K (K≥1) preceding significant of these elements in K preceding elements of the cycle, counted out from number i.

12. The method according to claim 1, wherein the main direction of observation $\Theta_{main}$ takes one of the two values by $\Theta$ coordinate, respectively either $\Theta_{ini}$ or $\Theta_{fin}$, at that the spatial orientation of the aperture plane of the antenna remains unchanged in time.

13. The method according to claim 1, wherein the main direction of observation $\Theta_{main}$ takes any value of the $\Theta$ coordinate, which are within the sector $\Delta\Theta$, with the exception of $\Theta_{ini}$, $\Theta_{fin}$, at that the spatial orientation of the of the aperture plane of the antenna remains unchanged in time.

14. The method according to claim 13, wherein the main direction of observation $\Theta_{main}$ takes value by $\Theta$ coordinate outside the $\Delta\Theta$ sector, at that the spatial orientation of the aperture plane of the antenna remains unchanged in time, at simultaneous uniform linear movement of antenna in the same plane.

15. An imaging system comprising:
an antenna rotor comprising:
  a two-dimensional diffraction grating;
  a planar dielectric wave-guide;
  an irradiator; and
  a rotating waveguide transition; and
a multi-channel receiver;
wherein the imaging system is configured to allow first and second calibration standards to be introduced into the system during predetermined phases.

16. The imaging system according to claim 15, further comprising first and second noise generators configured to provide the first and second calibration standards, respectively.

17. The imaging system according to claim 16, wherein the second noise generator comprises the first noise generator and an attenuator.

18. The imaging system according to claim 16, further comprising at least one switch to enable selection between a received signal, the first calibration standard and the second calibration standard.

19. The imaging system according to claim 18, further comprising a low noise amplifier configured to amplify a received signal, wherein the low noise amplifier is prior to at least one of the at least one switch in order to reduce system noise.

20. The imaging system according to claim 19, further comprising a mixer configured to downconvert a received signal, wherein the low noise amplifier, the at least one switch and the mixer are prior to the rotating waveguide transition, and wherein the rotating waveguide transition is coaxial.

* * * * *